(12) United States Patent
Alzari et al.

(10) Patent No.: US 7,364,856 B2
(45) Date of Patent: Apr. 29, 2008

(54) PKNB KINASE AND PSTP PHOSPHATASE AND METHODS OF IDENTIFYING INHIBITORY SUBSTANCES

(75) Inventors: Pedro Alzari, Paris (FR); Brigitte Boitel, Cignaux (FR); Andrea Villarino, Florianopolis (BR); Pablo Fernandez, Paris (FR); Steward T. Cole, Clamart (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 11/195,739

(22) Filed: Aug. 3, 2005

(65) Prior Publication Data

US 2006/0019324 A1    Jan. 26, 2006

Related U.S. Application Data

(63) Continuation of application No. 10/892,170, filed on Jul. 16, 2004, now abandoned.

(60) Provisional application No. 60/487,943, filed on Jul. 18, 2003.

(51) Int. Cl.

| C12Q 1/68 | (2006.01) |
|---|---|
| C12Q 1/48 | (2006.01) |
| C12Q 1/40 | (2006.01) |
| C12Q 1/22 | (2006.01) |
| C12N 1/20 | (2006.01) |
| C12N 15/74 | (2006.01) |
| C07H 21/04 | (2006.01) |

(52) U.S. Cl. .................. 435/6; 435/69.1; 435/194; 435/252.3; 435/253.1; 435/320.1; 435/471; 435/15; 435/21; 435/32; 536/23.2

(58) Field of Classification Search ............... 536/23.1; 435/320.1, 252.3, 183, 91.1, 471, 6
See application file for complete search history.

(56) References Cited

U.S. PATENT DOCUMENTS

2004/0029129 A1 * 2/2004 Wang et al. .................. 435/6
2006/0019324 A1    1/2006 Alzari et al.

FOREIGN PATENT DOCUMENTS

| CA | WO 03/074728 A2 * | 9/2003 |
| CA | WO 03.074728 A2 * | 9/2003 |
| WO | WO 03/074728 * | 9/2003 |

OTHER PUBLICATIONS

Av-Gay et al., Expression and characterization of the *Mycobacterium tuberculosis* serine/threonine kinase PknB. Infn. Immun. 67(11): 5676-5682, 1999.*
Fleischman et al., Whole-Genome comparison of *Mycobacterium tuberculosis* clinical and laboratory strains. J. Bacteriol., 2002, vol. 184 (19): 5479-5490.*

Young et al., Structure of *Mycobacterium tuberculosis* PknB supports a universal activation mechanism for Ser/Thr protein kinases. Nature Structural Biology, 2003, vol. 10 (3): 168-174. published on line 27 Jan. 2003.*
Ortiz-Lombardia et al., Crystal structure of the catalytic domain of the PknB serine/Threonine kinase from *Mycobacterium tuberculosis*. JBC., 2003, vol. 278 (15): 13094-13100. published on line Jan. 27, 2003.*
Av-Gay et al., Expression and characterization of the *Mycobacterium tuberculosis* serine/threonine protein kinase PknB. Infn. Immun. 67(11): 5677-5682, 1999.*
Tracy A. Young, et al., "Structure of *Mycobacterium tuberculosis* PknB supports a universal activation mechanism for Ser/Thr protein kinases", Nature Structural Biology-Advance online publication, 2003.
Rachna Chaba, et al., "Evidence that a eukaryotic-type serine/threonine protein kinase from *Mycobacterium tuberculosis* regulates morphological changes associated with cell division", Eur. J. Biochem, 269, 1078-1085 (2002).
Liang Shi, et al., "The serine, threonine, and/or tyrosine-specific protein kinases and protein phosphatases of prokaryotic organisms: a family portrait", FEMS Microbiology Reviews 22 (1998) 229-253.
Yossef Av-Gay, et al., "Expression and Characterization of the *Mycobacterium tuberculosis* Serine/Threonine Protein Kinase PknB", Infection and Immunity, Nov. 1999, pp. 5676-5682.
Anil Koul, et al., "Cloning and Characterization of Secretory Tyrosine Phosphatases of *Mycobacterium tuberculosis*", Journal of Bacteriology, Oct. 2000, p. 5425-5432.
Tatiana A. Gaidenko, et al., "The PrpC Serine-Threonine Phosphatase and PrkC Kinase Have Opposing Physiological Roles in Stationary-Phase *Bacillus subtilis* Cells", Journal of Bacteriology, Nov. 2002, pp. 6109-6114.
Anil Koul, et al., "Serine/threonine protein kinases PknF and PknG of *Mycobacterium tuberculosis*: characterization and localization", Microbiology (2001), 147, pp. 2307-2314.
Miguel Ortiz-Lombardia, et al., "Crystal Structure of the Catalytic Domain of the PknB Serine/Threonine Kinase from *Mycobacterium tuberculosis*", The Journal of Biological Chemistry, vol. 278, No. 15, Issue of Apr. 11, 2003, pp. 13094-13100.
Yossef Av-Gay, et al., "The eukaryotic-like Ser/Thr protein kinases of *Mycobacterium tuberculosis*", Trends in Microbiology, vol. 8, No. 5, May 2000.
Mark Pallen, et al., "Bacterial FHA domains: neglected players in the phosphor-threonine signaling game?", Trends in Microbiology, vol. 10, No. 12, Dec. 2002.
U.S. Appl. No. 10/564,975, filed Jan. 18, 2006, Alzari et al.

* cited by examiner

*Primary Examiner*—Rebecca E Prouty
*Assistant Examiner*—Ganapathirama Raghu
(74) *Attorney, Agent, or Firm*—Oblon, Spivak, McClelland, Maier & Neustadt, P.C.

(57) ABSTRACT

The present invention relates to a pknB kinase and a pstP phosphatase as well as their use for identifying antibacterial substances.

12 Claims, 12 Drawing Sheets

SEQUENCE LISTING

<160> NUMBER OF SEQ ID NOS: 20

<210> SEQ ID NO 1
<211> LENGTH: 514
<212> TYPE: PRT
<213> ORGANISM: Mycobacterium tuberculosis

<400> SEQUENCE: 1

```
Met Ala Arg Val Thr Leu Val Leu Arg Tyr Ala Ala Arg Ser Asp Arg
1               5                   10                  15

Gly Leu Val Arg Ala Asn Asn Glu Asp Ser Val Tyr Ala Gly Ala Arg
            20                  25                  30
```

-continued

```
Leu Leu Ala Leu Ala Asp Gly Met Gly Gly His Ala Ala Gly Glu Val
             35                  40                  45
Ala Ser Gln Leu Val Ile Ala Ala Leu Ala His Leu Asp Asp Asp Glu
         50                  55                  60
Pro Gly Gly Asp Leu Leu Ala Lys Leu Asp Ala Ala Val Arg Ala Gly
 65                  70                  75                  80
Asn Ser Ala Ile Ala Ala Gln Val Glu Met Glu Pro Asp Leu Glu Gly
                 85                  90                  95
Met Gly Thr Thr Leu Thr Ala Ile Leu Phe Ala Gly Asn Arg Leu Gly
            100                 105                 110
Leu Val His Ile Gly Asp Ser Arg Gly Tyr Leu Leu Arg Asp Gly Glu
            115                 120                 125
Leu Thr Gln Ile Thr Lys Asp Asp Thr Phe Val Gln Thr Leu Val Asp
            130                 135                 140
Glu Gly Arg Ile Thr Pro Glu Glu Ala His Ser His Pro Gln Arg Ser
145                 150                 155                 160
Leu Ile Met Arg Ala Leu Thr Gly His Glu Val Glu Pro Thr Leu Thr
                165                 170                 175
Met Arg Glu Ala Arg Ala Gly Asp Arg Tyr Leu Leu Cys Ser Asp Gly
            180                 185                 190
Leu Ser Asp Pro Val Ser Asp Glu Thr Ile Leu Glu Ala Leu Gln Ile
            195                 200                 205
Pro Glu Val Ala Glu Ser Ala His Arg Leu Ile Glu Leu Ala Leu Arg
            210                 215                 220
Gly Gly Pro Asp Asn Val Thr Val Val Ala Asp Val Val Asp
225                 230                 235                 240
Tyr Asp Tyr Gly Gln Thr Gln Pro Ile Leu Ala Gly Ala Val Ser Gly
                245                 250                 255
Asp Asp Asp Gln Leu Thr Leu Pro Asn Thr Ala Ala Gly Arg Ala Ser
            260                 265                 270
Ala Ile Ser Gln Arg Lys Glu Ile Val Lys Arg Val Pro Pro Gln Ala
            275                 280                 285
Asp Thr Phe Ser Arg Pro Arg Trp Ser Gly Arg Arg Leu Ala Phe Val
            290                 295                 300
Val Ala Leu Val Thr Val Leu Met Thr Ala Gly Leu Leu Ile Gly Arg
305                 310                 315                 320
Ala Ile Ile Arg Ser Asn Tyr Tyr Val Ala Asp Tyr Ala Gly Ser Val
                325                 330                 335
Ser Ile Met Arg Gly Ile Gln Gly Ser Leu Leu Gly Met Ser Leu His
            340                 345                 350
Gln Pro Tyr Leu Met Gly Cys Leu Ser Pro Arg Asn Glu Leu Ser Gln
            355                 360                 365
Ile Ser Tyr Gly Gln Ser Gly Gly Pro Leu Asp Cys His Leu Met Lys
            370                 375                 380
Leu Glu Asp Leu Arg Pro Pro Glu Arg Ala Gln Val Arg Ala Gly Leu
385                 390                 395                 400
Pro Ala Gly Thr Leu Asp Asp Ala Ile Gly Gln Leu Arg Glu Leu Ala
                405                 410                 415
Ala Asn Ser Leu Leu Pro Pro Cys Pro Ala Pro Arg Ala Thr Ser Pro
            420                 425                 430
Pro Gly Arg Pro Ala Pro Pro Thr Thr Ser Glu Thr Thr Glu Pro Asn
            435                 440                 445
```

```
Val Thr Ser Ser Pro Ala Ser Pro Ser Pro Thr Thr Ser Ala Pro Ala
    450                 455                 460

Pro Thr Gly Thr Thr Pro Ala Ile Pro Thr Ser Ala Ser Pro Ala Ala
465                 470                 475                 480

Pro Ala Ser Pro Pro Thr Pro Trp Pro Val Thr Ser Ser Pro Thr Met
                485                 490                 495

Ala Ala Leu Pro Pro Pro Pro Gln Pro Gly Ile Asp Cys Arg Ala
            500                 505                 510

Ala Ala

<210> SEQ ID NO 2
<211> LENGTH: 382
<212> TYPE: PRT
<213> ORGANISM: Homo sapiens

<400> SEQUENCE: 2

Met Gly Ala Phe Leu Asp Lys Pro Lys Met Glu Lys His Asn Ala Gln
1               5                   10                  15

Gly Gln Gly Asn Gly Leu Arg Tyr Gly Leu Ser Ser Met Gln Gly Trp
            20                  25                  30

Arg Val Glu Met Glu Asp Ala His Thr Ala Val Ile Gly Leu Pro Ser
        35                  40                  45

Gly Leu Glu Ser Trp Ser Phe Phe Ala Val Tyr Asp Gly His Ala Gly
    50                  55                  60

Ser Gln Val Ala Lys Tyr Cys Cys Glu His Leu Leu Asp His Ile Thr
65                  70                  75                  80

Asn Asn Gln Asp Phe Lys Gly Ser Ala Gly Ala Pro Ser Val Glu Asn
                85                  90                  95

Val Lys Asn Gly Ile Arg Thr Gly Phe Leu Glu Ile Asp Glu His Met
            100                 105                 110

Arg Val Met Ser Glu Lys Lys His Gly Ala Asp Arg Ser Gly Ser Thr
        115                 120                 125

Ala Val Gly Val Leu Ile Ser Pro Gln His Thr Tyr Phe Ile Asn Cys
    130                 135                 140

Gly Asp Ser Arg Gly Leu Leu Cys Arg Asn Arg Lys Val His Phe Phe
145                 150                 155                 160

Thr Gln Asp His Lys Pro Ser Asn Pro Leu Glu Lys Glu Arg Ile Gln
                165                 170                 175

Asn Ala Gly Gly Ser Val Met Ile Gln Arg Val Asn Gly Ser Leu Ala
            180                 185                 190

Val Ser Arg Ala Leu Gly Asp Phe Asp Tyr Lys Cys Val His Gly Lys
        195                 200                 205

Gly Pro Thr Glu Gln Leu Val Ser Pro Glu Pro Glu Val His Asp Ile
    210                 215                 220

Glu Arg Ser Glu Glu Asp Asp Gln Phe Ile Ile Leu Ala Cys Asp Gly
225                 230                 235                 240

Ile Trp Asp Val Met Gly Asn Glu Glu Leu Cys Asp Phe Val Arg Ser
                245                 250                 255

Arg Leu Glu Val Thr Asp Asp Leu Glu Lys Val Cys Asn Glu Val Val
            260                 265                 270

Asp Thr Cys Leu Tyr Lys Gly Ser Arg Asp Asn Met Ser Val Ile Leu
        275                 280                 285

Ile Cys Phe Pro Asn Ala Pro Lys Val Ser Pro Glu Ala Val Lys Lys
    290                 295                 300
```

```
Glu Ala Glu Leu Asp Lys Tyr Leu Glu Cys Arg Val Glu Glu Ile Ile
305                 310                 315                 320

Lys Lys Gln Gly Glu Gly Val Pro Asp Leu Val His Val Met Arg Thr
                325                 330                 335

Leu Ala Ser Glu Asn Ile Pro Ser Leu Pro Pro Gly Gly Glu Leu Ala
                340                 345                 350

Ser Lys Arg Asn Val Ile Glu Ala Val Tyr Asn Arg Leu Asn Pro Tyr
                355                 360                 365

Lys Asn Asp Asp Thr Asp Ser Thr Ser Thr Asp Met Trp
                370                 375                 380

<210> SEQ ID NO 3
<211> LENGTH: 271
<212> TYPE: PRT
<213> ORGANISM: Mycobacterium tuberculosis

<400> SEQUENCE: 3

Ile Thr Arg Asp Val Gln Val Pro Asp Val Arg Gly Gln Ser Ser Ala
1               5                   10                  15

Asp Ala Ile Ala Thr Leu Gln Asn Arg Gly Phe Lys Ile Arg Thr Leu
                20                  25                  30

Gln Lys Pro Asp Ser Thr Ile Pro Pro Asp His Val Ile Gly Thr Asp
                35                  40                  45

Pro Ala Ala Asn Thr Ser Val Ser Ala Gly Asp Glu Ile Thr Val Asn
        50                  55                  60

Val Ser Thr Gly Pro Glu Gln Arg Glu Ile Pro Asp Val Ser Thr Leu
65              70                  75                  80

Thr Tyr Ala Glu Ala Val Lys Lys Leu Thr Ala Ala Gly Phe Gly Arg
                85                  90                  95

Phe Lys Gln Ala Asn Ser Pro Ser Thr Pro Glu Leu Val Gly Lys Val
                100                 105                 110

Ile Gly Thr Asn Pro Pro Ala Asn Gln Thr Ser Ala Ile Thr Asn Val
                115                 120                 125

Val Ile Ile Ile Val Gly Ser Gly Pro Ala Thr Lys Asp Ile Pro Asp
        130                 135                 140

Val Ala Gly Gln Thr Val Asp Val Ala Gln Lys Asn Leu Asn Val Tyr
145                 150                 155                 160

Gly Phe Thr Lys Phe Ser Gln Ala Ser Val Asp Ser Pro Arg Pro Ala
                165                 170                 175

Gly Glu Val Thr Gly Thr Asn Pro Pro Ala Gly Thr Thr Val Pro Val
                180                 185                 190

Asp Ser Val Ile Glu Leu Gln Val Ser Lys Gly Asn Gln Phe Val Met
                195                 200                 205

Pro Asp Leu Ser Gly Met Phe Trp Val Asp Ala Glu Pro Arg Leu Arg
        210                 215                 220

Ala Leu Gly Trp Thr Gly Met Leu Asp Lys Gly Ala Asp Val Asp Ala
225                 230                 235                 240

Gly Gly Ser Gln His Asn Arg Val Val Tyr Gln Asn Pro Pro Ala Gly
                245                 250                 255

Thr Gly Val Asn Arg Asp Gly Ile Ile Thr Leu Arg Phe Gly Gln
                260                 265                 270

<210> SEQ ID NO 4
<211> LENGTH: 271
<212> TYPE: PRT
<213> ORGANISM: Mycobacterium leprae
```

<400> SEQUENCE: 4

```
Asn Thr Arg Asp Val Gln Val Pro Asp Val Arg Gly Gln Val Ser Ala
1               5                   10                  15
Asp Ala Ile Ser Ala Leu Gln Asn Arg Gly Phe Lys Thr Arg Thr Leu
            20                  25                  30
Gln Lys Pro Asp Ser Thr Ile Pro Pro Asp His Val Ile Ser Thr Glu
        35                  40                  45
Pro Gly Ala Asn Ala Ser Val Gly Ala Gly Asp Glu Ile Thr Ile Asn
    50                  55                  60
Val Ser Thr Gly Pro Glu Gln Arg Glu Val Pro Asp Val Ser Ser Leu
65                  70                  75                  80
Asn Tyr Thr Asp Ala Val Lys Lys Leu Thr Ser Ser Gly Phe Lys Ser
                85                  90                  95
Phe Lys Gln Ala Asn Ser Pro Ser Thr Pro Glu Leu Leu Gly Lys Val
            100                 105                 110
Ile Gly Thr Asn Pro Ser Ala Asn Gln Thr Ser Ala Ile Thr Asn Val
        115                 120                 125
Ile Thr Ile Ile Val Gly Ser Gly Pro Glu Thr Lys Gln Ile Pro Asp
    130                 135                 140
Val Thr Gly Gln Ile Val Glu Ile Ala Gln Lys Asn Leu Asn Val Tyr
145                 150                 155                 160
Gly Phe Thr Lys Phe Ser Gln Ala Ser Val Asp Ser Pro Arg Pro Thr
                165                 170                 175
Gly Glu Val Ile Gly Thr Asn Pro Pro Lys Asp Ala Thr Val Pro Val
            180                 185                 190
Asp Ser Val Ile Glu Leu Gln Val Ser Lys Gly Asn Gln Phe Val Met
        195                 200                 205
Pro Asp Leu Ser Gly Met Phe Trp Ala Asp Ala Glu Pro Arg Leu Arg
    210                 215                 220
Ala Leu Gly Trp Thr Gly Val Leu Asp Lys Gly Pro Asp Val Asp Ala
225                 230                 235                 240
Gly Gly Ser Gln His Asn Arg Val Ala Tyr Gln Asn Pro Pro Ala Gly
                245                 250                 255
Ala Gly Val Asn Arg Asp Gly Ile Ile Thr Leu Lys Phe Gly Gln
            260                 265                 270
```

<210> SEQ ID NO 5
<211> LENGTH: 274
<212> TYPE: PRT
<213> ORGANISM: Corynebacterium glutamicum

<400> SEQUENCE: 5

```
Ser Thr Ala Thr Ser Ala Ile Pro Asn Val Glu Gly Leu Pro Gln Gln
1               5                   10                  15
Glu Ala Leu Thr Glu Leu Gln Ala Ala Gly Phe Val Val Asn Ile Val
            20                  25                  30
Glu Glu Ala Ser Ala Asp Val Ala Glu Gly Leu Val Ile Arg Ala Asn
        35                  40                  45
Pro Ser Val Gly Ser Glu Ile Arg Gln Gly Ala Thr Val Thr Ile Thr
    50                  55                  60
Val Ser Thr Gly Arg Glu Met Ile Asn Ile Pro Asp Val Ser Gly Met
65                  70                  75                  80
Thr Leu Glu Asp Ala Ala Arg Ala Leu Glu Asp Val Gly Leu Ile Leu
                85                  90                  95
```

```
Asn Gln Asn Val Arg Glu Glu Thr Ser Asp Asp Val Glu Ser Gly Leu
            100                 105                 110
Val Ile Asp Gln Asn Pro Glu Ala Gly Gln Glu Val Val Gly Ser
        115                 120                 125
Ser Val Ser Leu Thr Met Ser Ser Gly Thr Glu Ser Ile Arg Val Pro
    130                 135                 140
Asn Leu Thr Gly Met Asn Trp Ser Gln Ala Gln Asn Leu Ile Ser
145                 150                 155                 160
Met Gly Phe Asn Pro Thr Ala Ser Tyr Leu Asp Ser Ser Pro Glu
                165                 170                 175
Gly Glu Val Leu Ser Val Ser Ser Gln Gly Thr Glu Leu Pro Lys Gly
            180                 185                 190
Ser Ser Ile Thr Val Glu Val Ser Asn Gly Met Leu Ile Gln Ala Pro
            195                 200                 205
Asp Leu Ala Arg Met Ser Thr Glu Gln Ala Ile Ser Ala Leu Arg Ala
            210                 215                 220
Ala Gly Trp Thr Ala Pro Asp Gln Ser Leu Ile Val Gly Asp Pro Ile
225                 230                 235                 240
His Thr Ala Ala Leu Val Asp Gln Asn Lys Ile Gly Phe Gln Ser Pro
                245                 250                 255
Thr Pro Ala Thr Leu Phe Arg Lys Asp Ala Gln Val Gln Val Arg Leu
                260                 265                 270
Phe Glu

<210> SEQ ID NO 6
<211> LENGTH: 268
<212> TYPE: PRT
<213> ORGANISM: Thermobifida fusca

<400> SEQUENCE: 6

Gly Arg Tyr Glu Thr Val Pro Asp Leu Val Gly Val Glu Ser Asp Glu
1               5                   10                  15
Ala Arg Arg Asp Leu Arg Met Leu Gly Phe Arg Val Gln Thr Ala Glu
            20                  25                  30
Glu Pro Ala Tyr Ser Asp Glu Ala Pro Pro Gly Thr Val Ala Ala Thr
        35                  40                  45
Asp Pro Glu Ala Gly Ser Arg Leu Leu Pro Asp Thr Leu Val Thr Leu
    50                  55                  60
Ile Leu Ser Ala Gly Pro Gln Tyr Val Glu Met Pro Asp Val Glu Gly
65                  70                  75                  80
Ala Ser Val Ala Glu Ala Arg Asp Ala Leu Lys Glu Val Gly Leu Thr
                85                  90                  95
Asp Ile Val Glu Asp Glu Ile Thr Ser Phe Asp Asn Pro Pro Gly Thr
            100                 105                 110
Val Ile Thr Thr Lys Pro Ala Pro Gly Glu Lys Ala Asn Arg Glu Glu
        115                 120                 125
Ser Val Thr Leu Thr Ile Ser Ala Gly Phe Pro Met Pro Asn Val Val
    130                 135                 140
Gly Gln Lys Val Asp Asp Ala Arg Arg Leu Leu Glu Ser Ser Asp Leu
145                 150                 155                 160
Glu Val Thr Val Val Glu Glu His His Asp Glu Val Pro Glu Gly His
                165                 170                 175
Val Ile Ser Gln Glu Pro Glu Ala Glu Thr Thr Val Gly Ala Gly Gln
            180                 185                 190
```

```
Ser Val Thr Leu Thr Val Ser Ser Gly Pro Glu Leu Glu Val Pro
            195                 200                 205

Asp Ile Arg Gly Trp Lys Val Asp Lys Ala Arg Lys Glu Leu Glu Glu
210                 215                 220

Arg Gly Phe Glu Val Thr Val His Gln Val Ile Gly Asn Arg Val Gly
225                 230                 235                 240

Asp Tyr Asn Pro Lys Gly Glu Ala Pro Lys Gly Ser Thr Ile Glu Ile
            245                 250                 255

Trp Thr Ser Pro Phe Gly Arg Glu Arg Asp Arg Asp
            260                 265
```

<210> SEQ ID NO 7
<211> LENGTH: 274
<212> TYPE: PRT
<213> ORGANISM: Corynebacterium efficiens

<400> SEQUENCE: 7

```
Ser Ala Ser Thr Gln Gln Ile Pro Asn Ile Val Gly Leu Pro Glu Asn
1               5                   10                  15

Glu Ala Val Leu Glu Leu Glu Arg Leu Gly Phe Thr Val Val Leu Thr
            20                  25                  30

Thr Glu Pro Ser Pro Asp Val Ala Glu Gly Leu Val Ile Arg Thr Ser
        35                  40                  45

Pro Asn Val Gly Ser Glu Ile Arg Glu Gly Ala Thr Val Thr Leu Thr
    50                  55                  60

Ile Ser Ser Gly Arg Glu Val Val Thr Ile Pro Asp Val Thr Gly Leu
65                  70                  75                  80

Thr Leu Ala Glu Ala Thr Arg Glu Ile Glu Gly Ala Gly Leu Val Leu
                85                  90                  95

Asp Gln Ser Ile Arg Glu Glu Asn Ser Asp Asp Tyr Pro Ala Gly Thr
            100                 105                 110

Val Ile Gln Gln Asn Pro Arg Ala Gly Gly Glu Thr Ser Val Gly Ala
        115                 120                 125

Ser Ile Thr Leu Thr Val Ser Thr Gly Pro Ser Leu Val Arg Val Pro
    130                 135                 140

Val Ile Thr Gly Met Gln Trp Ser Gln Ala Glu Ser Asn Ile Thr Ser
145                 150                 155                 160

Leu Gly Leu Val Pro Asp Ile Tyr Tyr Val Asp Ser Leu Leu Pro Glu
                165                 170                 175

Gly Gln Val Ile Ser Ala Ser Gly Gln Gly Thr Glu Leu Pro Arg Gly
            180                 185                 190

Ser Thr Val Thr Val Glu Ile Ser Asn Gly Met Leu Ile Glu Ala Pro
        195                 200                 205

Asp Leu Ala Arg Leu Asp Val Asp Asn Ala Leu Lys Ala Leu Arg Asp
    210                 215                 220

Ala Gly Trp Thr Ala Pro Asp Thr Ser Leu Ile Glu Gly Ala Pro Ile
225                 230                 235                 240

Pro Thr Gly Ala Leu Val Asp Gln Gly Arg Ile Gly Phe Gln Asp Pro
                245                 250                 255

Ser Pro Gly Gln Pro Leu Arg Lys Asp Ala Val Val Asn Ile Arg Leu
            260                 265                 270

Tyr Arg
```

<210> SEQ ID NO 8

```
<211> LENGTH: 212
<212> TYPE: PRT
<213> ORGANISM: Thermobifida fusca

<400> SEQUENCE: 8

Gly Thr Asp Asn Ile Thr Ile Pro Asn Val Ala Gly Met Ser Val Glu
1               5                   10                  15

Glu Ala Thr Glu Thr Leu Gln Glu Lys Gly Phe Glu Asn Ile Glu Val
            20                  25                  30

Ala Asp Glu Pro Thr Pro Ser Asn Glu Ile Glu Gly Lys Val Val
        35                  40                  45

Gly Thr Asp Pro Glu Ile Gly Glu Thr Val Pro Asp Thr Glu Ile
50                  55                  60

Thr Ile Leu Ile Ser Gly Gly Pro Glu Met Ile Glu Met Pro Asp Leu
65                  70                  75                  80

Val Gly Met Ser Gln Ala Asp Ala Leu Gly Glu Ile Asn Arg Ala Gly
                85                  90                  95

Leu Ala Arg Gly Glu Ile Thr His Gln Glu Ser Asp Glu Pro Gln Gly
            100                 105                 110

Thr Val Leu Ser Thr Asp Pro Lys Ala Gly Thr Glu Val Glu Pro Gly
        115                 120                 125

Thr Lys Val Asn Leu Val Val Ala Lys Ala Ser Thr Lys Val Glu Val
130                 135                 140

Pro Ser Leu Ala Gly Met Asn Glu Asp Gln Ala Arg Glu Arg Leu Ala
145                 150                 155                 160

Glu Leu Gly Leu Thr Leu Glu Ala Gln Thr Gln Glu Thr Ser Asp Ala
                165                 170                 175

Thr Pro Gly Thr Ala Ile Ala Gln Ser Pro Gln Ala Gly Thr Lys Val
            180                 185                 190

Glu Arg Gly Thr Thr Val Thr Val Thr Phe Ala Lys Glu Pro Gln Arg
        195                 200                 205

Pro Glu Pro Pro
    210

<210> SEQ ID NO 9
<211> LENGTH: 278
<212> TYPE: PRT
<213> ORGANISM: Bifidobacterium longum

<400> SEQUENCE: 9

Ser Glu Asp Thr Val Thr Ile Pro Glu Val Cys Asn Ala Ser Thr Ser
1               5                   10                  15

Lys Asp Ser Ile Glu Leu Lys Leu Lys Ala Ser Gly Leu Lys Met Thr
            20                  25                  30

Glu Lys Gln Asp Thr Asp Ser Thr Glu Pro Glu Gly Thr Cys Thr Lys
        35                  40                  45

Met Ser Pro Asp Ala Gly Ser Lys Val Ala Lys Gly Ser Ala Val Lys
    50                  55                  60

Val Trp Phe Ser Ala Gly Pro Gln Ser Thr Gln Val Pro Asp Val Lys
65                  70                  75                  80

Glu Arg Ser Gln Glu Glu Ala Arg Ser Ile Leu Glu Ser Ala Gly Phe
                85                  90                  95

Lys Val Asn Ala Ala Val Lys Thr Glu Asp Ser Ala Asp Ile Ala Lys
            100                 105                 110

Asp Met Val Thr Lys Thr Asp Pro Ala Ala Gly Gln Ser Val Pro Lys
        115                 120                 125
```

```
Gly Thr Thr Ile Thr Ile Tyr Val Ser Ser Gly Met Thr Thr Val Pro
        130                 135                 140

Ser Asn Leu Val Gly Gln Ser Lys Asp Ser Val Leu Gln Gln Tyr Glu
145                 150                 155                 160

Gly Lys Phe Ser Phe Thr Val Glu Gln Glu Ser Ser Asp Thr Val Glu
                165                 170                 175

Ala Gly Leu Ile Thr Arg Val Ser Pro Asp Ser Gly Ser Ser Ile Ala
            180                 185                 190

Gln Gly Gly Phe Ile Thr Ile Trp Val Ser Thr Gly Lys Glu Lys Val
        195                 200                 205

Ala Val Pro Asn Ile Thr Ala Gly Thr Asp Tyr Val Thr Ala Glu Leu
    210                 215                 220

Met Leu Lys Ala Val Gly Leu Lys Ala Gln Ala Asn Gly Pro Thr Gly
225                 230                 235                 240

Ser Thr Ala Val Val Ser Ile Asn Pro Gly Ala Gly Ser Gln Val
                245                 250                 255

Asp Ala Gly Ser Thr Val Thr Ile Thr Thr Lys Ala Gly Ser Thr Gly
            260                 265                 270

Gly Gly Thr Gly Thr Gly
        275

<210> SEQ ID NO 10
<211> LENGTH: 268
<212> TYPE: PRT
<213> ORGANISM: Streptomyces coelicolor

<400> SEQUENCE: 10

Ser Gly Gln Phe Thr Lys Val Pro Pro Leu Leu Ser Lys Thr Glu Ala
1               5                   10                  15

Gln Ala Arg Asp Arg Leu Asp Asp Ala Gly Leu Asp Val Gly Lys Val
            20                  25                  30

Arg His Ala Tyr Ser Asp Thr Val Glu Arg Gly Lys Val Ile Ser Thr
        35                  40                  45

Asp Pro Gly Val Gly Asp Arg Ile Arg Lys Asn Asp Ser Val Ser Leu
    50                  55                  60

Thr Val Ser Asp Gly Pro Asp Thr Val Lys Leu Pro Asp Val Thr Gly
65                  70                  75                  80

Tyr Lys Leu Asp Lys Ala Arg Thr Leu Leu Glu Asp Glu Gly Leu Glu
                85                  90                  95

Pro Gly Met Val Thr Arg Ala Phe Ser Asp Glu Val Ala Arg Gly Phe
            100                 105                 110

Val Ile Ser Thr Lys Pro Gly Ser Gly Thr Thr Val Arg Ala Gly Ser
        115                 120                 125

Ala Val Ala Leu Val Val Ser Lys Gly Ser Pro Val Asp Val Pro Asp
    130                 135                 140

Val Thr Gly Asp Asp Leu Asp Glu Ala Arg Ala Glu Leu Glu Gly Ala
145                 150                 155                 160

Gly Leu Lys Val Lys Thr Ala Asp Glu Arg Val Asn Ser Glu Tyr Asp
                165                 170                 175

Ser Gly Arg Val Ala Arg Gln Thr Pro Glu Pro Gly Gly Arg Ala Ala
            180                 185                 190

Glu Gly Asp Thr Val Thr Leu Thr Val Ser Lys Gly Pro Arg Met Ile
        195                 200                 205

Glu Val Pro Asp Val Val Gly Asp Ser Val Asp Asp Ala Lys Gln Lys
```

```
                    210                 215                 220
Leu Glu Asp Ala Gly Phe Glu Val Asp Glu Asp Arg Gly Leu Leu Gly
225                 230                 235                 240

Leu Phe Gly Asp Thr Val Lys Lys Gln Ser Val Asp Gly Gly Asp Thr
                245                 250                 255

Ala Pro Glu Gly Ser Thr Val Thr Ile Thr Ile Arg
                260                 265

<210> SEQ ID NO 11
<211> LENGTH: 279
<212> TYPE: PRT
<213> ORGANISM: Streptomyces coelicolor

<400> SEQUENCE: 11

Gly Asn Asp Lys Val Pro Val Pro Ala Phe Ile Gly Leu Ser Lys Ala
1               5                   10                  15

Asp Ala Gln Gln Gln Ala Asp Asn Ile Asp Leu Val Leu Thr Phe Lys
                20                  25                  30

Gln Gln Glu Cys Glu Asp Gln Pro Lys Gly Asn Ile Cys Ala Gln Asp
            35                  40                  45

Pro Lys Gln Gly Thr Asp Val Asp Lys Glu Ser Thr Val Asn Leu Val
        50                  55                  60

Val Ser Thr Gly Ala Pro Lys Val Ala Val Pro Asn Val Ile Asp Lys
65                  70                  75                  80

Asn Ile Asp Glu Ala Lys Lys Gln Leu Glu Asp Lys Gly Phe Glu Val
                85                  90                  95

Glu Thr Lys Gln Thr Glu Ser Ser Gln Asp Glu Gly Thr Ile Leu Ser
                100                 105                 110

Gln Asn Pro Asp Pro Gly Lys Glu Leu Glu Lys Gly Ser Thr Val Thr
            115                 120                 125

Leu Glu Val Ala Lys Ala Glu Glu Lys Ala Thr Val Pro Asp Val Val
        130                 135                 140

Gly Arg Thr Cys Asp Glu Ala Lys Ala Gln Val Glu Ser Gly Gly Asp
145                 150                 155                 160

Leu Thr Ala Val Cys Thr Asp Gln Pro Thr Asn Asp Pro Asn Gln Val
                165                 170                 175

Gly Lys Val Ile Ser Thr Thr Pro Gln Ser Ser Thr Gln Val Asp Pro
                180                 185                 190

Gly Ser Lys Val Thr Ile Val Val Gly Lys Ala Val Glu Lys Thr Lys
            195                 200                 205

Val Pro Glu Val Arg Gly Lys Thr Leu Ala Glu Ala Arg Gln Ile Leu
        210                 215                 220

Gln Gln Ser Gly Phe Thr Asn Val Gln Val Ala Gln Gly Ser Pro Gly
225                 230                 235                 240

Asp Asp Asn Ala Lys Val Phe Ala Ser Asn Pro Gln Pro Gly Ser Glu
                245                 250                 255

Val Asp Asp Pro Ala Ala Thr Pro Ile Thr Leu Met Thr Val Pro Gly
                260                 265                 270

Asp Gly Gly Asn Gly Asn Gly
        275

<210> SEQ ID NO 12
<211> LENGTH: 277
<212> TYPE: PRT
<213> ORGANISM: Bacillus subtilis
```

```
<400> SEQUENCE: 12

Met Pro Lys Asp Val Lys Ile Pro Asp Val Ser Gly Met Glu Tyr Glu
1               5                   10                  15

Lys Ala Ala Gly Leu Leu Glu Lys Glu Gly Leu Gln Val Asp Ser Glu
            20                  25                  30

Val Leu Glu Ile Ser Asp Glu Lys Ile Glu Glu Gly Leu Met Val Lys
        35                  40                  45

Thr Asp Pro Lys Ala Asp Thr Thr Val Lys Glu Gly Ala Thr Val Thr
    50                  55                  60

Leu Tyr Lys Ser Thr Gly Lys Ala Lys Thr Glu Ile Gly Asp Val Thr
65                  70                  75                  80

Gly Gln Thr Val Asp Gln Ala Lys Lys Ala Leu Lys Asp Gln Gly Phe
                85                  90                  95

Asn His Val Thr Val Asn Glu Val Asn Asp Glu Lys Asn Ala Gly Thr
            100                 105                 110

Val Ile Asp Gln Asn Pro Ser Ala Gly Thr Glu Leu Val Pro Ser Glu
        115                 120                 125

Asp Gln Val Lys Leu Thr Val Ser Ile Gly Pro Glu Asp Ile Thr Leu
    130                 135                 140

Arg Asp Leu Lys Thr Tyr Ser Lys Glu Ala Ala Ser Gly Tyr Leu Glu
145                 150                 155                 160

Asp Asn Gly Leu Lys Leu Val Glu Lys Glu Ala Tyr Ser Asp Asp Val
                165                 170                 175

Pro Glu Gly Gln Val Val Lys Gln Lys Pro Ala Ala Gly Thr Ala Val
            180                 185                 190

Lys Pro Gly Asn Glu Val Glu Val Thr Phe Ser Leu Gly Pro Glu Lys
        195                 200                 205

Lys Pro Ala Lys Thr Val Lys Glu Lys Val Lys Ile Pro Tyr Glu Pro
    210                 215                 220

Glu Asn Glu Gly Asp Glu Leu Gln Val Gln Ile Ala Val Asp Asp Ala
225                 230                 235                 240

Asp His Ser Ile Ser Asp Thr Tyr Glu Glu Phe Lys Ile Lys Glu Pro
                245                 250                 255

Thr Glu Arg Thr Ile Glu Leu Lys Ile Glu Pro Gly Gln Lys Gly Tyr
            260                 265                 270

Tyr Gln Val Met Val
        275

<210> SEQ ID NO 13
<211> LENGTH: 16
<212> TYPE: PRT
<213> ORGANISM: Mycobacterium tuberculosis

<400> SEQUENCE: 13

Gly Ser Ser His His His His His His Ser Ser Gly Leu Val Pro Arg
1               5                   10                  15

<210> SEQ ID NO 14
<211> LENGTH: 28
<212> TYPE: PRT
<213> ORGANISM: Mycobacterium tuberculosis

<400> SEQUENCE: 14

Ala Ile Ala Asp Ser Gly Asn Ser Val Pro Gln Thr Ala Ala Val Ile
1               5                   10                  15

Gly Thr Ala Gln Tyr Leu Ser Pro Glu Gln Ala Arg
```

-continued

```
<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 15
gatagccata tgaccacccc ttcc                                          24

<210> SEQ ID NO 16
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 16
aaaccgaagc ttaacggccc accg                                          24

<210> SEQ ID NO 17
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 17
cgggggcata tggcgcgcgt ga                                            22

<210> SEQ ID NO 18
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 18
gcagtcgtaa gcttatgccg ccg                                           23

<210> SEQ ID NO 19
<211> LENGTH: 469
<212> TYPE: PRT
<213> ORGANISM: Mycobacterium tuberculosis

<400> SEQUENCE: 19
```

Met Thr Thr Arg Leu Gln Ala Pro Val Ala Val Thr Pro Pro Leu Pro
1               5                   10                  15

Thr Arg Arg Asn Ala Glu Leu Leu Leu Leu Cys Phe Ala Ala Val Ile
            20                  25                  30

Thr Phe Ala Ala Leu Leu Val Val Gln Ala Asn Gln Asp Gln Gly Val
        35                  40                  45

Pro Trp Asp Leu Thr Ser Tyr Gly Leu Ala Phe Leu Thr Leu Phe Gly
    50                  55                  60

Ser Ala His Leu Ala Ile Arg Arg Phe Ala Pro Tyr Thr Asp Pro Leu
65                  70                  75                  80

Leu Leu Pro Val Val Ala Leu Leu Asn Gly Leu Gly Leu Val Met Ile
                85                  90                  95

His Arg Leu Asp Leu Val Asp Asn Glu Ile Gly Glu His Arg His Pro
            100                 105                 110

```
Ser Ala Asn Gln Gln Met Leu Trp Thr Leu Val Gly Val Ala Ala Phe
            115                 120                 125

Ala Leu Val Val Thr Phe Leu Lys Asp His Arg Gln Leu Ala Arg Tyr
    130                 135                 140

Gly Tyr Ile Cys Gly Leu Ala Gly Leu Val Phe Leu Ala Val Pro Ala
145                 150                 155                 160

Leu Leu Pro Ala Ala Leu Ser Glu Gln Asn Gly Ala Lys Ile Trp Ile
                165                 170                 175

Arg Leu Pro Gly Phe Ser Ile Gln Pro Ala Glu Phe Ser Lys Ile Leu
            180                 185                 190

Leu Leu Ile Phe Phe Ser Ala Val Leu Val Ala Lys Arg Gly Leu Phe
        195                 200                 205

Thr Ser Ala Gly Lys His Leu Leu Gly Met Thr Leu Pro Arg Pro Arg
    210                 215                 220

Asp Leu Ala Pro Leu Leu Ala Ala Trp Val Ile Ser Val Gly Val Met
225                 230                 235                 240

Val Phe Glu Lys Asp Leu Gly Ala Ser Leu Leu Tyr Thr Ser Phe
                245                 250                 255

Leu Val Val Val Tyr Leu Ala Thr Gln Arg Phe Ser Trp Val Val Ile
                260                 265                 270

Gly Leu Thr Leu Phe Ala Ala Gly Thr Leu Val Ala Tyr Phe Ile Phe
            275                 280                 285

Glu His Val Arg Leu Arg Val Gln Thr Trp Leu Asp Pro Phe Ala Asp
        290                 295                 300

Pro Asp Gly Thr Gly Tyr Gln Ile Val Gln Ser Leu Phe Ser Phe Ala
305                 310                 315                 320

Thr Gly Gly Ile Phe Gly Thr Gly Leu Gly Asn Gly Gln Pro Asp Thr
                325                 330                 335

Val Pro Ala Ala Ser Thr Asp Phe Ile Ile Ala Ala Phe Gly Glu Glu
            340                 345                 350

Leu Gly Leu Val Gly Leu Thr Ala Ile Leu Met Leu Tyr Thr Ile Val
        355                 360                 365

Ile Ile Arg Gly Leu Arg Thr Ala Ile Ala Thr Arg Asp Ser Phe Gly
    370                 375                 380

Lys Leu Leu Ala Ala Gly Leu Ser Ser Thr Leu Ala Ile Gln Leu Phe
385                 390                 395                 400

Ile Val Val Gly Gly Val Thr Arg Leu Ile Pro Leu Thr Gly Leu Thr
                405                 410                 415

Thr Pro Trp Met Ser Tyr Gly Gly Ser Ser Leu Leu Ala Asn Tyr Ile
            420                 425                 430

Leu Leu Ala Ile Leu Ala Arg Ile Ser His Gly Ala Arg Arg Pro Leu
        435                 440                 445

Arg Thr Arg Pro Arg Asn Lys Ser Pro Ile Thr Ala Ala Gly Thr Glu
    450                 455                 460

Val Ile Glu Arg Val
465
```

<210> SEQ ID NO 20
<211> LENGTH: 491
<212> TYPE: PRT
<213> ORGANISM: Mycobacterium tuberculosis

<400> SEQUENCE: 20

```
Met Asn Ala Ser Leu Arg Arg Ile Ser Val Thr Val Met Ala Leu Ile
1               5                   10                  15
```

```
Val Leu Leu Leu Leu Asn Ala Thr Met Thr Gln Val Phe Thr Ala Asp
             20                  25                  30

Gly Leu Arg Ala Asp Pro Arg Asn Gln Arg Val Leu Leu Asp Glu Tyr
             35                  40                  45

Ser Arg Gln Arg Gly Gln Ile Thr Ala Gly Gly Gln Leu Leu Ala Tyr
 50                      55                  60

Ser Val Ala Thr Asp Gly Arg Phe Arg Phe Leu Arg Val Tyr Pro Asn
 65                  70                  75                  80

Pro Glu Val Tyr Ala Pro Val Thr Gly Phe Tyr Ser Leu Arg Tyr Ser
                 85                  90                  95

Ser Thr Ala Leu Glu Arg Ala Glu Asp Pro Ile Leu Asn Gly Ser Asp
             100                 105                 110

Arg Arg Leu Phe Gly Arg Arg Leu Ala Asp Phe Phe Thr Gly Arg Asp
             115                 120                 125

Pro Arg Gly Gly Asn Val Asp Thr Thr Ile Asn Pro Arg Ile Gln Gln
         130                 135                 140

Ala Gly Trp Asp Ala Met Gln Gln Gly Cys Tyr Gly Pro Cys Lys Gly
145                 150                 155                 160

Ala Val Val Ala Leu Glu Pro Ser Thr Gly Lys Ile Leu Ala Leu Val
                 165                 170                 175

Ser Ser Pro Ser Tyr Asp Pro Asn Leu Leu Ala Ser His Asn Pro Glu
             180                 185                 190

Val Gln Ala Gln Ala Trp Gln Arg Leu Gly Asp Asn Pro Ala Ser Pro
             195                 200                 205

Leu Thr Asn Arg Ala Ile Ser Glu Thr Tyr Pro Pro Gly Ser Thr Phe
         210                 215                 220

Lys Val Ile Thr Thr Ala Ala Leu Ala Ala Gly Ala Thr Glu Thr
225                 230                 235                 240

Glu Gln Leu Thr Ala Ala Pro Thr Ile Pro Leu Pro Gly Ser Thr Ala
                 245                 250                 255

Gln Leu Glu Asn Tyr Gly Gly Ala Pro Cys Gly Asp Glu Pro Thr Val
             260                 265                 270

Ser Leu Arg Glu Ala Phe Val Lys Ser Cys Asn Thr Ala Phe Val Gln
         275                 280                 285

Leu Gly Ile Arg Thr Gly Ala Asp Ala Leu Arg Ser Met Ala Arg Ala
         290                 295                 300

Phe Gly Leu Asp Ser Pro Arg Pro Thr Pro Leu Gln Val Ala Glu
305                 310                 315                 320

Ser Thr Val Gly Pro Ile Pro Asp Ser Ala Ala Leu Gly Met Thr Ser
                 325                 330                 335

Ile Gly Gln Lys Asp Val Ala Leu Thr Pro Leu Ala Asn Ala Glu Ile
             340                 345                 350

Ala Ala Thr Ile Ala Asn Gly Gly Ile Thr Met Arg Pro Tyr Leu Val
         355                 360                 365

Gly Ser Leu Lys Gly Pro Asp Leu Ala Asn Ile Ser Thr Thr Val Gly
 370                     375                 380

Tyr Gln Gln Arg Arg Ala Val Ser Pro Gln Val Ala Ala Lys Leu Thr
385                 390                 395                 400

Glu Leu Met Val Gly Ala Glu Lys Val Ala Gln Gln Lys Gly Ala Ile
                 405                 410                 415

Pro Gly Val Gln Ile Ala Ser Lys Thr Gly Thr Ala Glu His Gly Thr
             420                 425                 430
```

-continued

```
Asp Pro Arg His Thr Pro Pro His Ala Trp Tyr Ile Ala Phe Ala Pro
        435                 440                 445

Ala Gln Ala Pro Lys Val Ala Val Ala Val Leu Val Glu Asn Gly Ala
    450                 455                 460

Asp Arg Leu Ser Ala Thr Gly Gly Ala Leu Ala Ala Pro Ile Gly Arg
465                 470                 475                 480

Ala Val Ile Glu Ala Ala Leu Gln Gly Glu Pro
                485                 490
```

PKNB KINASE AND PSTP PHOSPHATASE AND METHODS OF IDENTIFYING INHIBITORY SUBSTANCES

CROSS-REFERENCE TO RELATED APPLICATIONS

The present application is a continuation of U.S. application Ser. No. 10/892,170 filed Jul. 16, 2004, abandoned, and claims the benefit of U.S. provisional application Ser. No. 60/487,943 filed Jul. 18, 2003.

BACKGROUND OF THE INVENTION

1. Field of the Invention

The present invention relates to a pknB kinase and a pstP phosphatase as well as their use for identifying antibacterial substances.

2. Description of the Background

Tuberculosis (TB) is a major public health problem with one-third of the world's population infected by its aetiologic agent, *Mycobacterium tuberculosis*, and over two million people dying from the disease each year (Dye et al., 1999, *WHO Global Surveillance Monitoring Project J Am Med Assoc* 282: 677-686). The Global Alliance for TB Drug Development has proposed that the current treatment could be improved considerably by developing more potent therapeutic agents, that reduce the duration of therapy, and by including drugs that act on latent bacilli (Global Alliance for TB Drug Development. (2001) Scientific blueprint for tuberculosis drug development. *Tuberculosis* 81: 1-52.). Faced with the urgency to develop new therapeutic strategies, it appears crucial to understand better the physiopathology of the causative agent and its complex relationship with the immune system of the host.

After inhalation, infectious bacilli are phagocytosed by alveolar macrophages in the lung and induce a local pro-inflammatory response, which leads to the recruitment of monocytes from the bloodstream into the site of infection (Dannenberg, A. M. (1999) Pathophysiology: basic aspects. In *Tuberculosis and Nontuberculous Mycobacterial Infections*. Schlossberg, D., (ed.). Philadelphia: W.B. Saunders Company, pp. 17-47; Russell, 2001, *Nature Rev Mol Cell Biol* 2: 569-577). By blocking fusion of phagosomes with lysosomes in these non-activated macrophages (Brown et al., 1969, *Nature* 221: 658-660; Sturgill-Koszycki et al., 1996, *EMBO J* 15: 6960-6968), *M. tuberculosis* escapes killing and multiplies. As the immune response progresses, macrophages and T cells accumulate to form a granuloma in which the pathogen is contained in a latent state (Parrish et al., 1998, *TIBS* 6: 107-112; Manabe and Bishai, 2000, *Nature Med* 6: 1327-1329). It can lie dormant for years only to rise again when the immune system wanes through old age, malnutrition or AIDS (acquired immuno-deficiency syndrome). The centre of the granuloma then liquefies and *M. tuberculosis* replicates profusely and is discharged into the bronchial tree producing an infectious cough (Dannenberg, 1999, Pathophysiology: basic aspects. In *Tuberculosis and Nontuberculous Mycobacterial Infections*. Schlossberg, D., (ed.). Philadelphia: W.B. Saunders Company, pp. 17-47). To understand the bacterial response to these changes in host environment, the study of regulatory proteins involved in mycobacterial signal transduction is therefore of the utmost importance.

Phosphorylation, a simple and efficient means of reversibly changing the biochemical properties of a protein, is a major mechanism for signal transduction and regulation of almost all biological functions. There are two main phosphorylative signal transduction systems. Prokaryotes predominantly use the two-component system, comprising in its simplest form a signal sensor with a histidine kinase domain and a response regulator, often a transcriptional factor (Wurgler-Murphy and Saito, 1997, *TIBS* 22: 172-176; Stock et al., 2000, *Annu Rev Biochem* 69: 183-215). This simple, unidirectional mechanism allows a quick response to abrupt environmental changes. The second system depends on the reversible phosphorylation of serine, threonine and tyrosine residues, and is widely used in eukaryotes (Hanks and Hunter, 1995, *FASEB J* 9: 576-596; Hunter, 1995, *Cell* 80: 225-236; Barford et al., 1998, *Annu Rev Biophys Biomol Struct* 27: 133-164; Hunter, 2000, *Cell* 100: 113-127). This mechanism involves the action of protein kinases and phosphoprotein phosphatases in cascades and networks (Hunter, 2000, *Cell* 100: 113-127), providing an efficient means for the rapid modulation of the transduced signal to serve highly regulated functions.

Since the identification of the first bacterial homologue a few years ago (Muñoz-Dorado et al., 1991, *Cell* 67: 995-1006), genomics has now demonstrated that serine, threonine and tyrosine protein kinases and phosphatases are also widespread in prokaryotes (Zhang, 1996, *Mol Microbiol* 20: 9-15; Kennelly, 2002, *FEMS Microbiol Lett* 206: 1-8). The two phosphorylation mechanisms (two-component systems and Ser/Thr/Tyr kinases and phosphatases) in prokaryotes may regulate distinct functions or act together in the same signalling pathway. The presence of Ser/Thr and Tyr kinases and phosphatases in prokaryotes appears to be associated with a complex, multistage developmental cycle and possible roles in regulating growth and development (heterocyst, fruiting-body or spore formation) have been proposed (Zhang, 1996, *Mol Microbiol* 20: 9-15; Shi et al., 1998, *FEMS Microbiol Rev* 22: 229-253). The dormant state of *M. tuberculosis*, although poorly understood, may be considered in some regards analogous to sporulation (Demaio et al., 1996, *Proc Natl Acad Sci USA* 93: 2790-2794) and thus involve these enzymes.

*Mycobacterium tuberculosis* employs both systems of protein phosphorylation. It has 15 sensor His kinases and 15 response regulators, forming at least 11 functional pairs, together with 11 putative Ser/Thr protein kinases (STPKs), one phospho-Ser/Thr phosphatase (ppp renamed here pstP) and two Tyr phosphatases (ptpA, ptpB) (Cole et al., 1998, *Nature* 393: 537-544). There appears to be no counterpart Tyr kinase for the two Tyr phosphatases, PtpA and PtpB, which can, moreover, be secreted (Koul et al., 2000, *Microbiology* 147: 2307-2314; Cowley et al., 2002, *Res Microbiol* 153: 233-241). Eight of the 11 STPKs are predicted to be transmembrane proteins, with a putative extracellular signal sensor domain and an intracellular kinase domain. Six STPKs (PknA, B, D, E, F, G) have already been expressed as recombinant proteins and shown to be functional kinases (Peirs et al., 1997, *Eur J Biochem* 244: 604-612; Av-Gay et al., 1999, *Infect Immun* 67: 5676-5682; Koul et al., 2001, *J Bacteriol* 182: 5425-5432; Chaba et al., 2002, *Eur J Biochem* 269: 1078-1085; data not shown for PknE).

At this time, no physiological role has been clearly demonstrated for any of the STPKs or phosphatases from *M. tuberculosis*, and knock-out mutants have not yet been reported.

In view of the above, there remains a need for developing new targets and therapies for mycobacterial infections.

SUMMARY OF THE INVENTION

B. Analysis of the specificity of $PstP_{1-240}$ towards phosphoresidues. MBP (left panel) and α-casein (right panel) were phosphorylated either on serine and threonine residues or on tyrosine residues with $[\gamma$-$^{33}P]ATP$. Release of radiolabelled inorganic phosphate was measured after incubation of increasing concentrations of the purified $PstP_{1-240}$ with the different phosphosubstrates.

FIG. 4: A. Structural organization of PknB. B. Sequence alignment of the putative sensor domain of bacterial STPKs. A BLAST search was conducted to detect the protein sequences most similar to the PknB C-terminal domain. We then selected among them the nine STPKs most similar to *M. tuberculosis* PknB, i.e. STPKs from *M. leprae, Corynebacterium glutamicum, C. efficiens, Thermobifida fusca, Bifidobacterium longum, Streptomyces coelicolor* and *Bacillus subtilis* (SEQ ID NOS:3-12). The sequences of the C-terminal domains of these proteins were aligned with CLUSTALW. The extracellular domain of these STPKs consists of three to four PASTA domains, represented as different blocks. These repeated domains may have arisen by duplication events.

Figure 5:
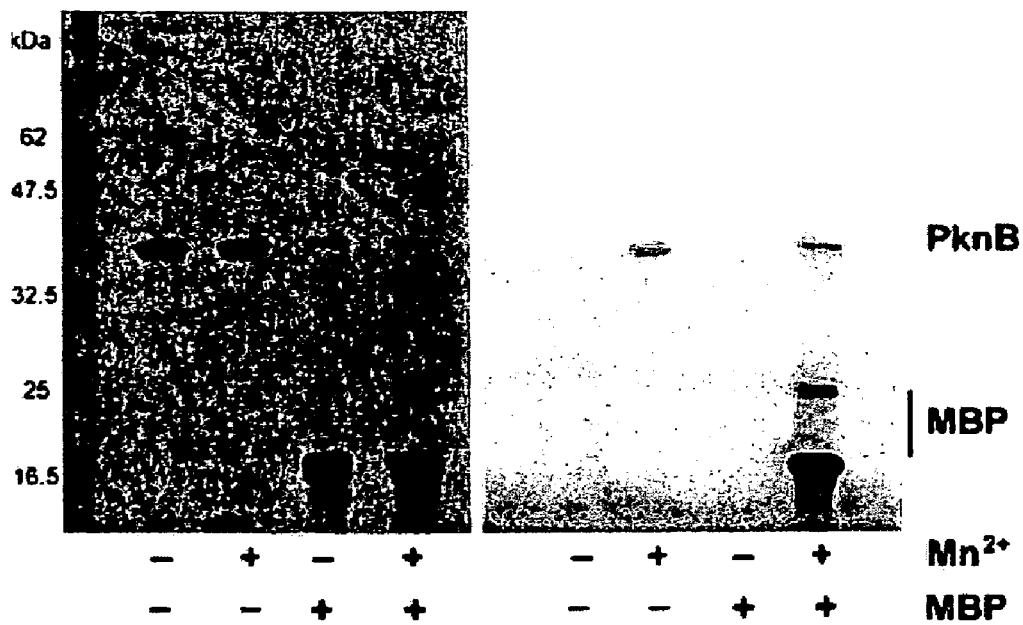
Figure 5:
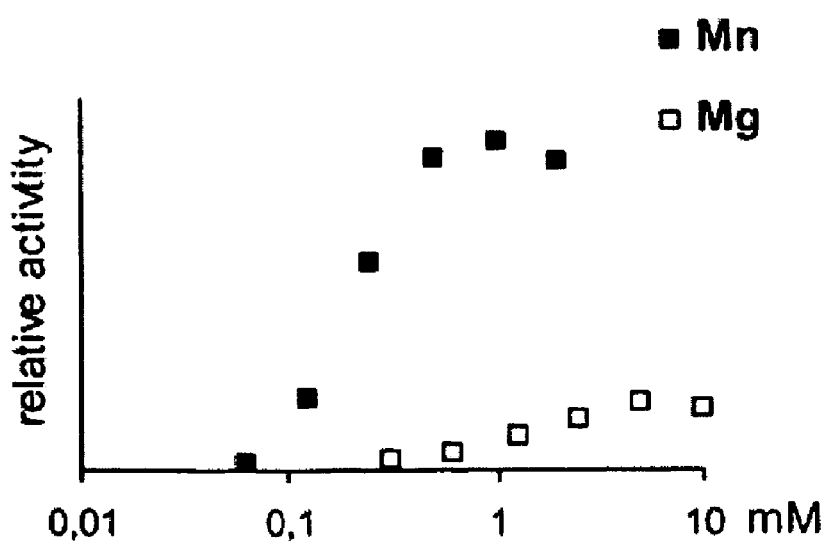

FIG. 5: A. Kinase activity of $PknB_{1-279}$: autophosphorylation and MBP phosphorylation assays. Purified $PknB_{1-279}$, alone or with the model kinase substrate MBP, was incubated with $[\gamma$-$^{33}P]ATP$ in the presence or absence of $MnCl_2$. The reaction products were resolved on a SDS-PAGE gel that was Coomassie blue stained (left panel) then dried and autoradiographied (right panel). As observed for other phosphoproteins, the apparent MW of the protein in SDS-PAGE (40 kDa) is significantly higher than the expected value of 32 kDa. Effect of divalent cations on the kinase activity of $PknB_{1-279}$. Various concentrations of $MnCl_2$ or $MgCl_2$ were used in the MBP phosphorylation assay. Relative quantification of the incorporated phosphate on MBP was obtained after PhosphorImager analysis.

Figure 6:
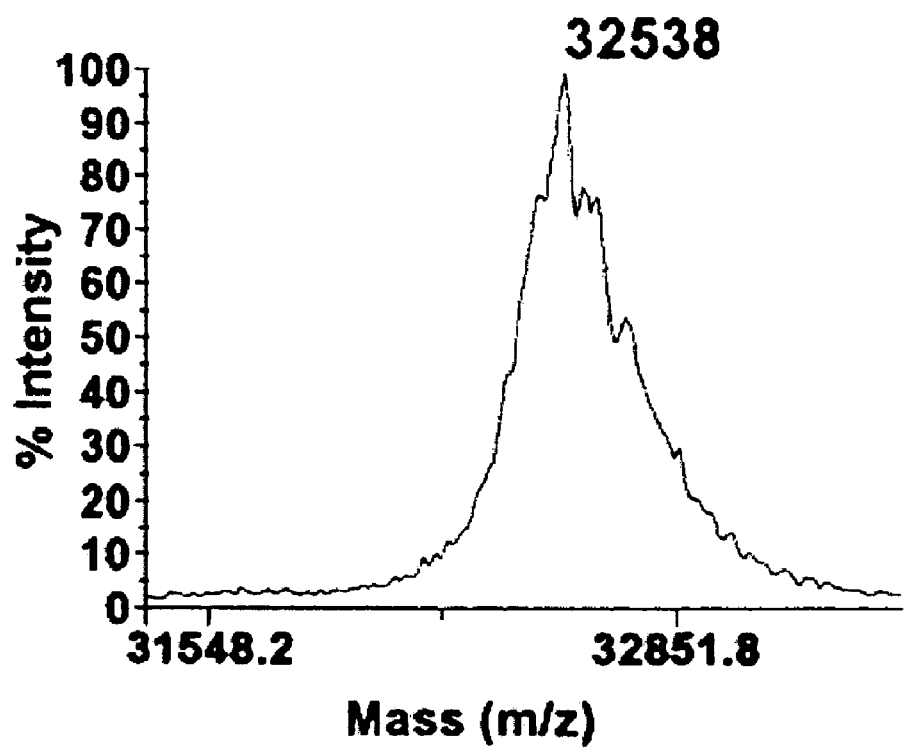
Figure 6:
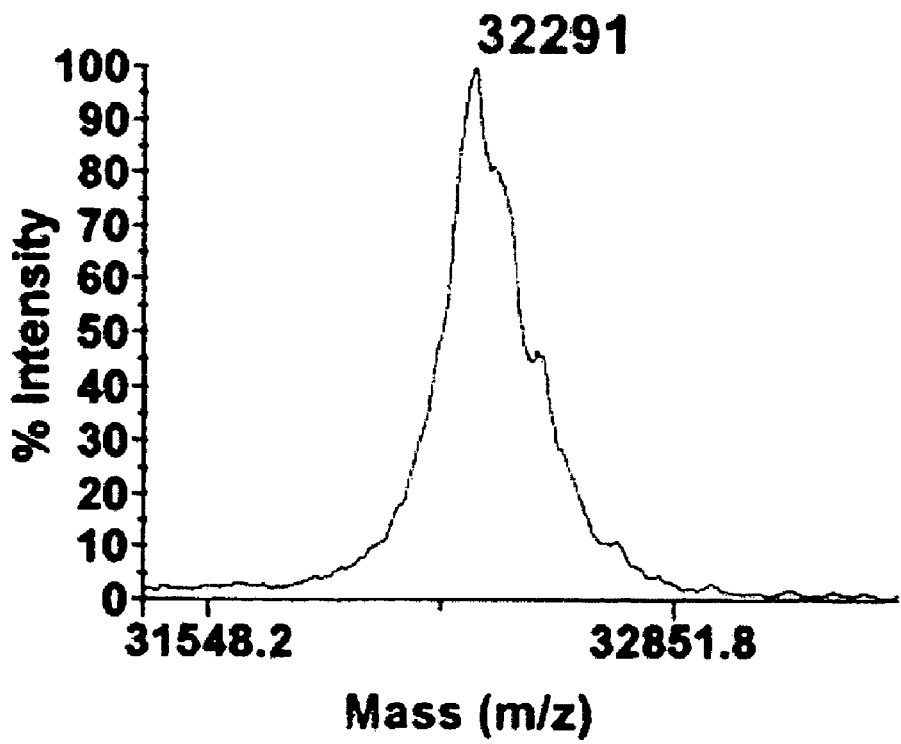

FIG. 6: MALDI spectra of PknB before (A) and after (B) dephosphorylation with alkaline phosphatase.

Figure 7:
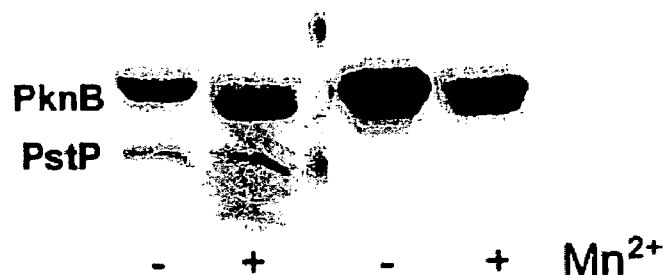
Figure 7:
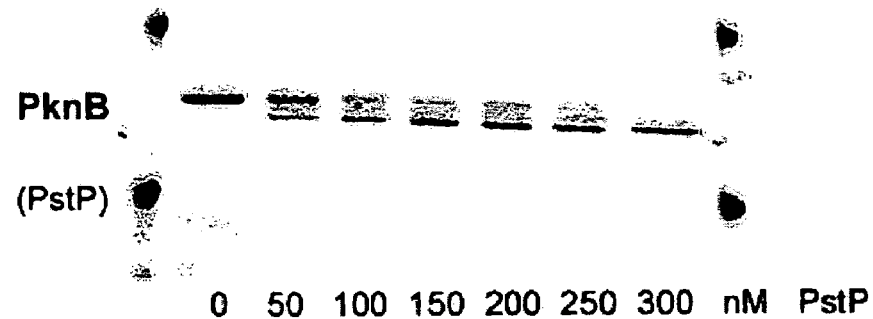
Figure 7:
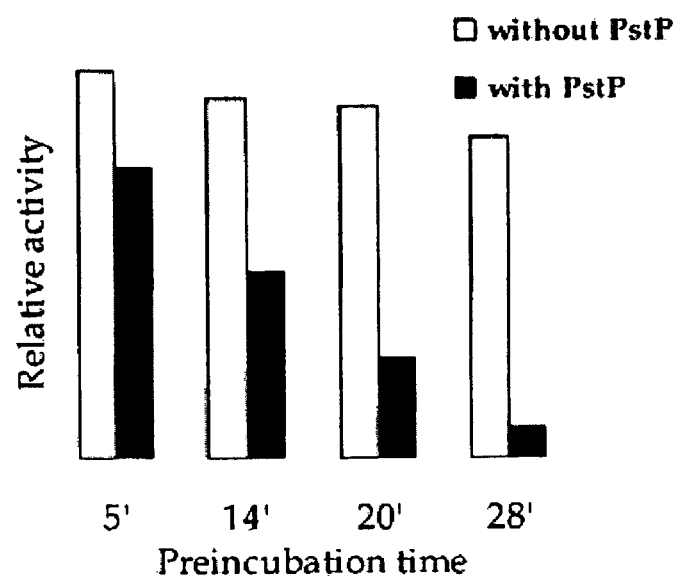

FIG. 7: Dephosphorylation assay using $PknB_{1-279}$ as a substrate for $PstP_{1-240}$ and effect of the dephosphorylation of $PknB_{1-279}$ by $PstP_{1-240}$ on its kinase activity.

A. Autophosphorylated $PknB_{1-279}$ in presence of $[\gamma$-$^{33}P]ATP$ was used as substrate for $PstP_{1-240}$. As a control, $MnCl_2$ was omitted from the reaction buffer. The products of the reaction were subjected to electrophoresis on a denaturing gel. Left panel: the Coomassie blue stained gel; right panel: the autoradiograph.

B. Without prior labelling, dephosphorylation of PknB is followed with the shift in protein migration in SDS-PAGE. $PknB_{1-279}$ was preincubated with $PstP_{1-240}$ for the indicated time. The kinase activity was then assayed using MBP and thio-γATP as substrates. Relative quantification of the kinase activity obtained with the PhosphorImager was plotted.

FIG. 8: Identification of phosphorylation sites in $PknB_{1-279}$.

A. HPLC separation of tryptic digests from $PknB_{1-279}$ before (upper panel) and after treatment with PstP (lower panel). Fractions were manually collected and analysed by MALDI-MS, with partial sequencing by PSD-MS when necessary for conclusive peptide identification. Only peptides relevant to this work are annotated in the chromatograms: peak 1, monophosphorylated His-tag peptide (m/z=1848.61, calc. monoisotopic mass=1848.84); peak 2, His-tag peptide (m/z=1768.91, calc. monoisotopic mass=1768.84, sequence GSSHHHHHHSSGLVPR-SEQ ID NO:13); peak 3, diphosphorylated S162-R189 peptide (m/z=2979.17, calc. monoisotopic mass=2979.34); and peak 4, S162-189 peptide (m/z=2819.53, calc. monoisotopic mass=2819.41).

B. Detailed PSD spectra obtained with a sample from peak 3. The signals corresponding to −80 Da, −98 Da, −(80+98) Da, −(98+98) Da are strongly indicative of presence of two phosphate groups in serine and/or threonine residues in the analysed sample.

C. Integrated PSD spectra to confirm peptide identification by sequencing (SEQ ID NO:14) and to localise phosphorylated residues (measured values from the y-ion series in Da: $y_3$=374.0; $y_5$=600.1; $y_6$=687.2; $y_7$=799.8; $y_8$=962.0; $y_9$=1091.0; $y_{10}$=1162.3; $y_{11}$=1262.5; $y_{12}$=1319.4; $y_{13}$=1433.1; $y_{14}$=1533.2; $y_{15}$=1603.3; $y_{16}$=1674.4; $y_{17}$−98=1757.3; $y_{18}$−98=1886.1; $y_{19}$−98−98=1969.0; $y_{19}$−98=2067.4; $y_{19}$=2165.4).

Figure 9:
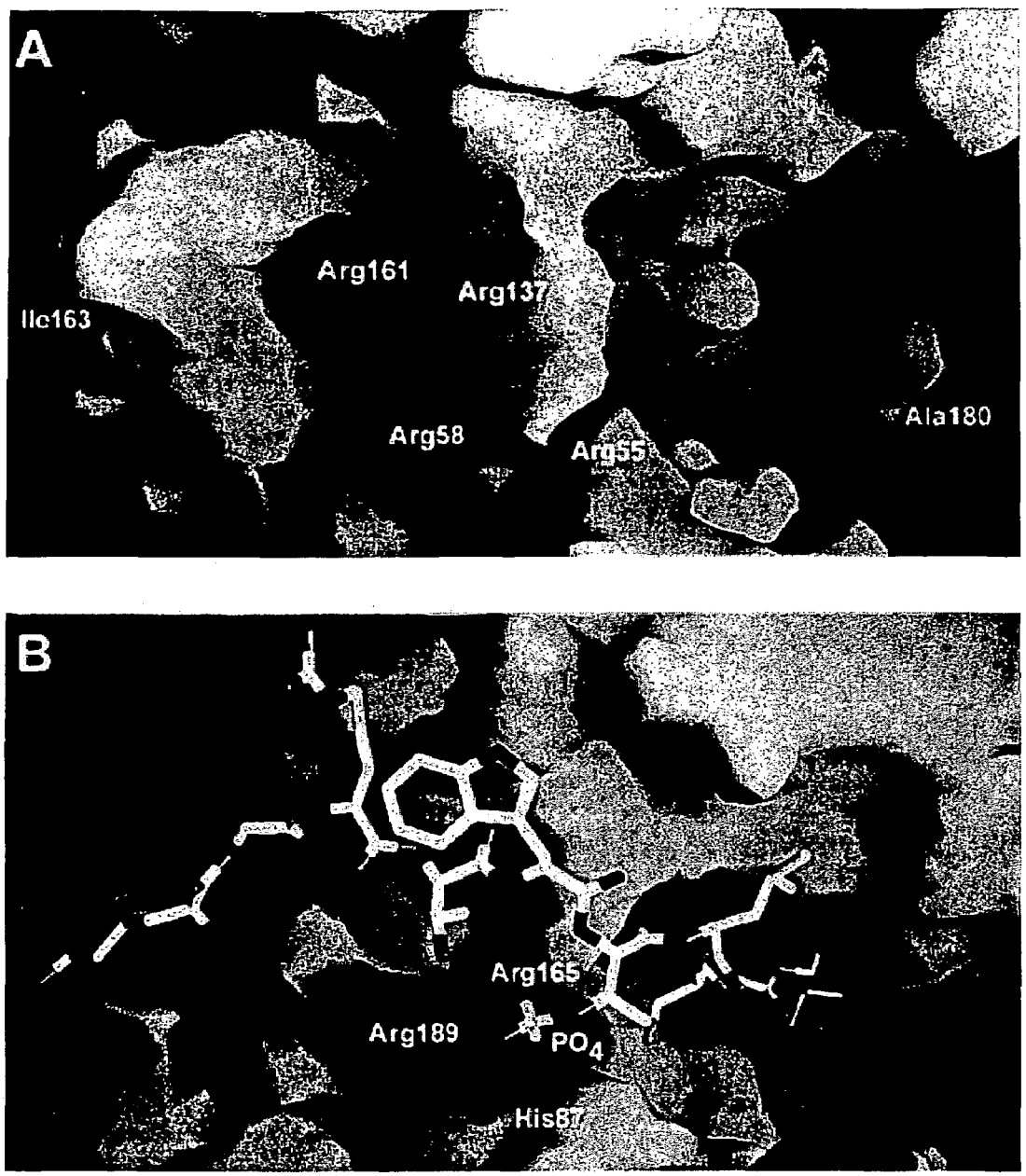

FIG. 9: The putative phosphate-binding site in PknB.

A. Surface representation of PknB (PDB code 1O6Y) colour-coded according to charge. A cluster of four exposed arginine residues could provide a binding site for the two phosphorylated threonine residues, Thr171 and Thr173. Sixteen residues from the activation loop (connecting Ile163 to Ala180 and including the two phosphothreonines) are disordered in the crystal structure.

B. Equivalent view of mouse PKA (PDB code 1ATP), in which the region corresponding to that missing in PknB is shown in stick representation. The phosphate group of phospho-Thr197 makes hydrogen-bonding interactions with the side chains of two arginine and one histidine residues.

Figure 10:
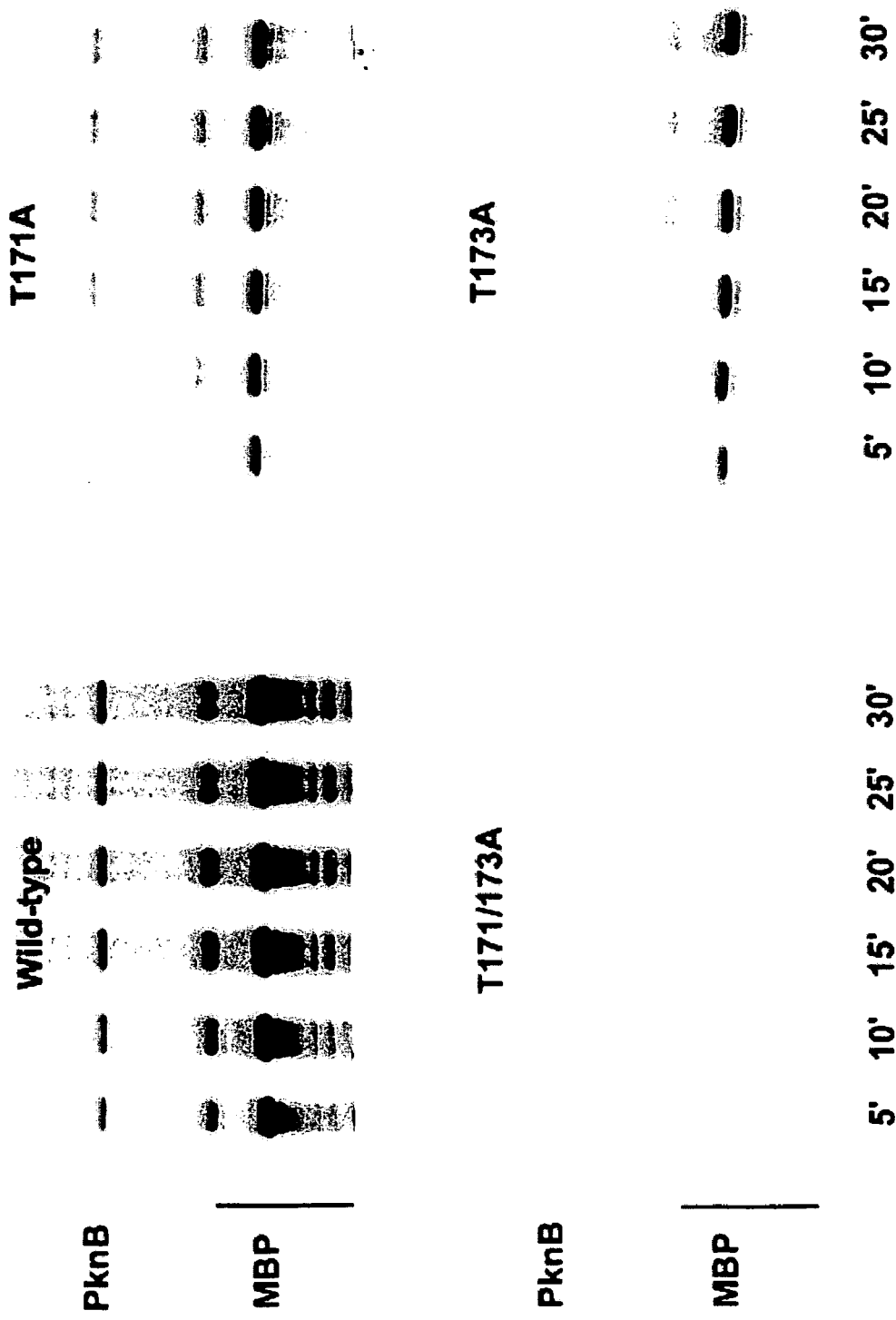

FIG. 10: Kinase activity of the activation loop mutants of PknB. MBP phosphorylation assays have been performed in parallel for the alanine mutants and the wild-type $PknB_{1-279}$. Relative quantification of the kinase activity was obtained with the PhosphorImager: T171A, T173A and T171/173 A mutants are ≈15, 20, and 300 times less active than $PknB_{1-279}$ respectively.

DETAILED DESCRIPTION OF THE INVENTION

The pknB and pstP genes along with pknA are found in an operon (FIG. 1) that also includes rodA and pbpA (Cole et al., 1998, *Nature* 393: 537-544), two genes encoding morphogenic proteins involved in peptidoglycan synthesis during cell growth (Matsuhashi, 1994, Utilization of lipid-linked precursors and the formation of peptidoglycan in the process of cell growth and division. In *Bacterial Cell Wall*. Ghuysen, J.-M., and Hakenbeck, R., (eds). Amsterdam-London: Elsevier). Furthermore, this genomic region remains unchanged in the close relative *M. leprae* (Fsihi et al., 1996, *Microbiology* 142: 3147-3161), in spite of the extensive gene decay in this *bacillus* which has removed or inactivated over 2400 genes including those for all other STPKs (except for PknL and PknG) and both Tyr phosphatases (Eiglmeier et al., 2001, *Leprosy Rev* 72: 387-398). Thus, the conservation of the pknA, pknB and pstP genes near the chromosomal origin of replication in *M. leprae* strongly suggests that the corresponding enzymes could regulate essential functions, possibly related to cell growth or latency of mycobacteria.

We demonstrate here that Pstp dephosphorylates specifically phospho-Ser/Thr residues and that its activity is strictly dependent on the presence of divalent cations. We also report that the catalytic domain of PknB, as defined by homology modelling, is an active protein kinase in its phosphorylated state. Pstp is capable of dephosphorylating PknB, which subsequently exhibits decreased kinase activity. Mass spectrometry analysis identified two phosphothreonine residues in the activation loop of PknB. Mutagenesis of these threonines in alanine demonstrate their role in regulating PknB kinase activity. Thus, Pstp and PknB could interplay in vivo in the same transduction pathway, and discuss the putative regulatory roles of these enzymes in mycobacteria.

Figure 1:
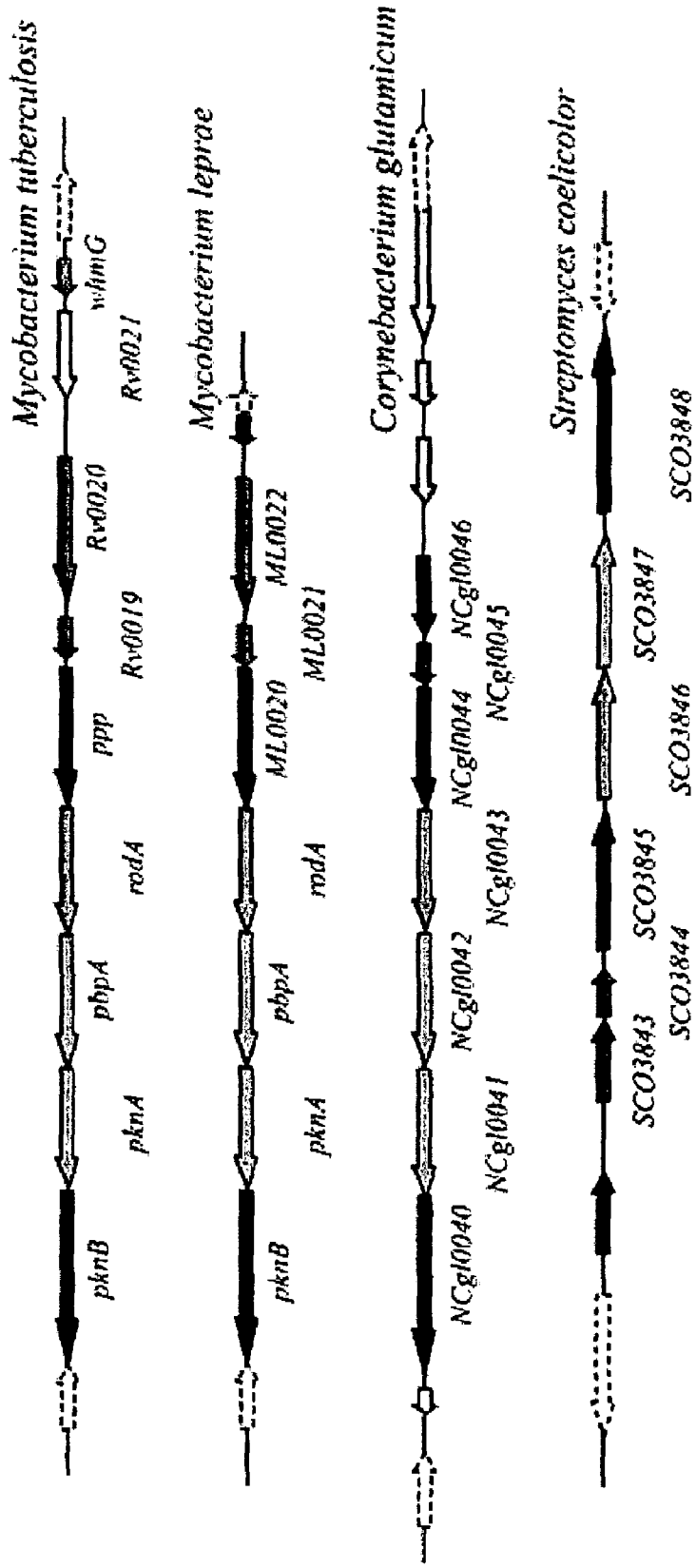
FIG. 1: Conserved structure of the putative operon including the pknB and pstP genes in several actinobacteria. The genes coding for the following signal tranduction elements, PknA, PknB, PstP and two proteins with a FHA domain, are co-localized with two genes involved in peptidoglycan synthesis, namely pbpA and rodA. This gene cluster is conserved in all actinobacteridae genomes known to date, including those presented here, *M. tuberculosis, M. leprae, C. glutamicum* and *S. coelicolor* (note that the pknA gene is missing in *S. coelicolor* genome) and also such as *C. diphteriae, C. efficiens, Thermobifida fusca* and *Bifidobacterium longum*.

In prokaryotes, genes involved in the same cellular process are frequently clustered often forming an operon. Thus, co-localization of the pknB and pstP genes in the same genomic region (FIG. 1) reinforces the hypothesis that these enzymes can intervene in the same signal transduction pathway. Furthermore, the organization of this genomic region suggests the participation of additional signal transduction elements, including a second STPK (namely PknA) and two proteins harbouring FHA domains (Rv0019c and Rv0020c), all of which are also conserved in other actinobacteria (FIG. 1). The FHA domains are small (Å130 aa) protein modules that mediate protein-protein interaction via the recognition of a phosphorylated threonine on the target molecule (Durocher and Jackson, 2002, *FEBS Lett* 513: 58-66). In eukaryotes, they are present in numerous signalling and regulatory proteins such as kinases, phosphatases, RNA-binding proteins and transcription factors. Rv0019c (155 aa) corresponds to a single FHA domain whereas Rv0020c (527 aa) has two domains, a Ct FHA domain and a Nt domain that shows no homology with any known protein except with its orthologue in *M. leprae* (ML0022). The FHA domain of Rv0020c has recently been characterized for its ability to bind phosphorylated peptide ligands (Durocher et al., 2000, *Mol Cell* 6: 1169-1182).

Also found in the same conserved operon (FIG. 1) are two genes, pbpA and rodA, encoding proteins involved in controlling cell shape and peptidoglycan synthesis during cell growth (Matsuhashi, 1994, Utilization of lipid-linked precursors and the formation of peptidoglycan in the process of cell growth and division. In *Bacterial Cell Wall*. Ghuysen, J.-M., and Hakenbeck, R., (eds). Amsterdam-London: Elsevier). Cell growth and development require the cell wall to have a dynamic structure. Indeed, the cell wall changes continuously, during growth and developmental processes such as sporulation, and in response to changes in the environment. Moreover, morphological adaptation like cell wall thickening could be an important determinant for survival of the slow-growing pathogenic mycobacteria in anaerobiosis (Cunningham and Spreadbury, 1998, *J Bacteriol* 180: 801-808). Cross-linked peptidoglycan, a major component of the bacterial cell wall, is synthesized by penicillin-binding proteins (PBP), which are membrane anchored enzymes with two external catalytic modules. Some PBPs are only involved in specific phases of growth or development and, for transglycosylase activity, they are each associated with a membrane protein partner. Thus in *E. coli*, PBP2 and RodA are responsible for peptidoglycan synthesis during cell elongation and for determination of the rod shape, whereas PBP3 and FtsW are involved in peptidoglycan synthesis during cell division (septation). In *B. subtilis*, a homologous couple (PBP and SpoVE) is thought to be engaged in spore formation.

Therefore, PknA, PknB and PstP, along with other signalling modulators, co-ordinately regulate cell elongation during growth. Indeed, recent data suggest a regulatory role for PknA in cell elongation (Chaba et al., 2002, *Eur J Biochem* 269: 1078-1085) and it has been speculated that the extracellular domain of PknB could bind unlinked peptidoglycan (Yeats et al., 2002, *TIBS* 27: 438-440). Kinases and phosphatase might have opposing effects on the control of such a complex integrated pathway. Tight regulation of the process of cell elongation could therefore be a key element in mycobacterial development and provide a link between the intra/extracellular growth phase and the latent lifestyle within the granuloma. The data presented herein support the targeting of the signaling modulators described herein for the development of antibacterial agents, e.g., antitubercular that are capable of targeting *M. tuberculosis* in the different stages of its life cycle.

The pstp2 phosphatase in the present invention comprises an amino acid sequence as set forth in SEQ ID NO:1. The pknB protein kinase in the present invention comprises an amino acid sequence as set forth in SEQ ID NO:3. Polynucleotides encoding the amino acid sequences can be readily ascertained using the known genetic code and degeneracy of the code.

In one embodiment, the proteins that are at least 70%, at least 80%, at least 90%, at least 95%, at least 97%, at least 98%, and at least 99% identical to the pstp2 and pknB amino acid sequences or the polynucleotides encoding the amino acid sequences described herein are also included in the present invention. Preferably, the proteins have protein kinase or phosphatase activity as appropriate according to the description herein. Such proteins retain at least 5%, 10%, 15%, 25%, 30%, 40%, 50%, 60%, 70%, 80%, 90% or can have greater than 100% of the protein kinase or phosphatase activities as described herein.

These polynucleotides can hybridize under stringent conditions to the coding polynucleotide sequences of the pknB and pstp2 amino acid sequences. The terms "stringent conditions" or "stringent hybridization conditions" includes reference to conditions under which a polynucleotide will hybridize to its target sequence, to a detectably greater degree than other sequences (e.g., at least 2-fold over background). High stringency conditions include hybridization in 50% formamide, 1 M NaCl, 1% SDS at 37° C., and a wash in 0.1×SSC at 60 to 65° C. Amino acid and polynucleotide identity, homology and/or similarity can be determined using the ClustalW algorithm, MEGALIGN™, Lasergene, Wis.).

The polynucleotides encoding the pknB and pstp2 proteins can be in a single polynucleotide molecule, e.g., a vector or in separate polynucleotide molecules. In one embodiment, the polynucleotides encoding the pknB and pstp2 proteins are present on one polynucleotide molecule, e.g., in a bacterial operon. A polynucleotide encoding the pknB and pstp2 proteins can also comprise rodA (SEQ ID NO:19) and/or pbpA genes (SEQ ID NO:20) in the same polynucleotide, e.g., vector. The polynucleotides may also be present in a recombinant bacterial host cell, for example, E. coli or mycobacterium (e.g., Mycobacterium tuberculosis). In such bacterial cells, the genes can be expressed from a single polynucleotide, e.g., vector or operon; or can be expressed separately from each other; as well as combinations of two or three with the remaining proteins being expressed on a separate polynucleotide.

One embodiment of the present invention is to screen for substances that modulate the activity of one or both of the pknB and pstp2 proteins described herein. Substances that modulate the activity of one or both of the pknB and pstp2 can be used as an antibacterial agent, and particularly, for treating infections caused by a mycobacterium such as, for example, Mycobacterium tuberculosis. The method of screening for substances comprises contacting a host cell comprising one or both of the pknB and pstp2 proteins described herein, measuring the protein kinase and/or phosphatase activity of one or both of the pknB and pstp2 proteins, and comparing the activity of one or both of the pknB and pstp2 proteins in the host cell prior to contacting or in a control host cell that has not been contacted with the substance. A change in relative activity of one or both of the pknB and pstp2 proteins indicates that the substance is effective in modulating those activities.

In another embodiment, the substances identified above, can be tested for antibacterial activity, for example, inhibiting mycobacterium, preferably M. tuberculosis. The method would involve contacting a cell or a population of cells to be tested with the substance and determine whether the growth and/or survival of the bacterial cell or cells are impaired compared to a cell or cells that are not contacted with the substance or the same bacterial cell or cells prior to being contacted with the substance. Any appreciable impairment is indicative that the substance possesses antibacterial activity.

The substance(s) identified above can be synthesized by any chemical or biological method.

The substance(s) identified above can be prepared in a formulation containing one or more known physiologically acceptable diluents and/or carriers. The substance can also be used or administered to a mammalian subject in need of antibacterial treatment, for example, a human infected with M. tuberculosis.

EXAMPLES

EXPERIMENTAL PROCEDURES

Sequence Analysis and Modeling

For biochemical and structural (Ortiz-Lombardía et al., 2003, J Biol Chem 278: 13094-13100) studies, the catalytic kinase core of PknB was originally defined using a homology modelling approach. The 10 closest sequences from the Protein Data Bank were selected, and a multiple alignment was carried out using CLUSTALW. After manual editing of the alignment, the five sequences sharing highest identity with PknB (namely C. elegans Twitchin kinase, rabbit phosphorylase kinase, mouse PKA, and human CDK6 and CDK2) were used as templates for homology modelling. Using different combinations of these templates various families of models were constructed and refined with the program MODELLER (v. 4.0). A comparison of the most self-consistent models allowed us to identify Gly 279 as the likely end point for the α-helix I defining the C-terminus of the kinase catalytic core.

Cloning and Mutagenesis

Cosmid MTCY10H4 containing pknB (Rv0014c) and pstP (Rv0018c) was used in subcloning experiments. A PknB construct corresponding to the putative cytoplasmic domain (catalytic domain+juxtamembrane sequence–aa 1-331) was first obtained, as some regions outside the kinase core could stabilize the catalytic domain. The following primers were used for PCR amplification: forward primer (with NdeI site): 5'-GATAGCCATATGACCACCCCTTCC-3' (SEQ ID NO:15) and reverse primer (5'-TAA codon +HindIII site): 5'-AAACCGAAGCTTAACGGC CCACCG-3' (SEQ ID NO:16). The digested and purified PCR product was ligated into the pET28 expression vector using the engineered NdeI and HindIII sites. $PknB_{1-331}$ was expressed as a broad heterogeneous protein, probably reflecting heterogeneity of its phosphorylation state as various phosphorylated residues were detected in the juxtamembrane region (data not shown). A shorter construct corresponding to the core catalytic domain (aa 1-279) was thus obtained, introducing a stop codon by site-directed mutagenesis. PknB mutants (T171A, T173A, T171/173 A) were all obtained from this last construct by the same method.

The complete pstP gene was subcloned into pET28 expression vector using the following primers: forward primer (with NdeI site): 5'-CGGGGGCATATGGC GCGCGTGA-3' (SEQ ID NO:17) and reverse primer (TAA codon +HindIII site): 5'-GCAGTCGTAAGCTTATGC-CGCCG-3' (SEQ ID NO:18). The construct corresponding to the catalytic domain of PstP (aa 1-240) was then obtained by introducing a stop codon through site-directed mutagenesis.

All mutagenesis was done according to the Quick Change Stratagene procedure. Enzymes were purchased as follows: the T4 DNA ligase, NdeI and DpnI restriction enzymes from Biolabs, HindIII and BglII restriction enzymes from Pharmacia, the Pfu and Pfu turbo polymerases from Stratagene. All constructs were verified by DNA sequencing.

Protein Expression and Purification

Escherichia coli BL21 (DE3) bacteria transformed with the appropriate plasmid were grown at 37° C. until late log phase in Luria-Bertani (LB) medium with antibiotic (kanamycin 30 μg ml$^{-1}$). Induction of expression was conducted for 12-16 h at low temperature (15° C.) after addition of 1 mM IPTG. Bacterial pellet was resuspended in 50 mM Hepes buffer pH 7, 0.2 M NaCl, in the presence of protease inhibitors and sonicated. The lysate was cleared by centrifugation (20 000 g, 30 min to 1 h). The supernatant containing soluble proteins was applied to Ni-column (Pharmacia) using an FPLC system and eluted by an imidazol gradient (0-0.5 M). A further step of gel filtration (Superdex 75) was required to separate the aggregated material from the monomeric proteins and to remove imidazol and most of the Ni$^{2+}$ cations. Proteins were subsequently concentrated by means of Macro- and Micro-sep concentrators (Pall/Gellman). Protein concentration was determined using the Bio-Rad protein assay. Purity of the samples was checked by SDS-PAGE electrophoresis.

Protein Kinase Assays

The kinase assays were carried out in 20 µl of kinase buffer (Hepes 50 mM pH 7, DTT 1 mM, Brij35 0.01%) containing 2 mM $MnCl_2$, 100 µM ATP and 1 µCi of [$\gamma$-$^{33}$P]-ATP. For the analysis of divalent cation preference various concentrations of $MnCl_2$ or $MgCl_2$ were used, as indicated in the FIG. 1B. For autophosphorylation 5 µM final of the purified PknB was used. For phosphorylation of the MBP substrate by PknB or the PknB mutants, the enzyme/substrate ratio was 1:20 with 0.5 µM kinase. The reaction was started with the addition of the kinase and conducted at 30° C. for 10 min. For the kinetics of MBP phosphorylation by PknB and the PknB mutants, 10 µl-aliquots of a scaled-up 60 µl reaction mixture were withdrawn at each indicated time. The reaction was stopped by the addition of SDS-PAGE sample buffer plus EDTA (25 mM final). Ten µl of the reaction were subjected to electrophoresis. In each case, the reaction products were separated on a 12% SDS-polyacrylamide gel and the radiolabelled proteins visualized by auto-radiography. To obtain relative quantification of the incorporation of radiolabelled ATP, the radioactive samples were also analysed using a PhosphorImager apparatus (STORM, Molecular Dynamics). For testing kinase activity of PknB after various incubation times with PstP, ATP and [$\gamma$-$^{33}$P]ATP were replaced by thio-$\gamma$ATP and [$^{35}$S]ATP-$\gamma$S respectively. [$\gamma$-$^{33}$P]ATP and [$^{35}$S]ATP-$\gamma$S were purchased from AmershamBiosciences. MBP was from Invitrogen.

Protein Phosphatase Assays

Dephosphorylation of phosphoSer/Thr or phosphoTyr proteins by PstP was assayed using either MBP or α-casein (SIGMA). Phosphorylated [$^{33}$P]Ser/Thr-substrates or [$^{33}$P]Tyr-substrates were prepared by phosphorylation of the proteins using either the catalytic subunit of PKA or the Abl protein tyrosine kinase. In each case, the kinase reaction was performed in 200 µl of buffer (50 mM Hepes pH 7.5, 5 mM $MgCl_2$, 1 mM EGTA, 2 mM DTT, 0.01% Brij35) with 1 mM ATP, 75 µCi [$\gamma$-$^{33}$P]ATP, 200 µM substrate and 25 units of PKA or 10 units of Abl kinase. The reaction was incubated for 5 h at 30° C. Phosphorylated substrate was recovered by TCA precipitation and extensively dialysed at 4° C. against a 25 mM Tris buffer pH 7.5 with 0.1 mM EDTA, 2 mM DTT and 0.01% Brij35. Dephosphorylation assays were carried out in a 25 µl reaction mixture containing 50 mM Hepes buffer pH 7.5, 0.1 mM EDTA, 1 mM DTT and 0.01% Brij35, 5 mM $MnCl_2$. Phosphorylated [$^{33}$P] substrates were used to a final concentration corresponding to 10 µM of incorporated phosphates. The reaction was started with the addition of various concentrations of the purified PstP (up to 200 ng/25 µl, ≈0.3 µM) and incubated for 10 min at 30° C. The reaction was terminated by adding cold 20% TCA. After centrifugation, soluble materials were added to scintillation fluid and counted for the release of inorganic phosphate. The serine/threonine phosphatase PP1 and the Tyrosine phosphatase T-Cell PTP were used as control for the dephosphorylation of the phosphoSer/Thr substrates and the phosphoTyr substrates, respectively (not shown). The dephosphorylation of PknB by PstP was first performed using autophosphorylated [$^{33}$P]-PknB that was prepared according to the above protocol, except that no extra kinase was added. The reaction was performed in 15 µl of Hepes buffer 50 mM pH 7, DTT 1 mM, Brij35 0.01% with 2 mM $MnCl_2$. [$^{33}$P]-PknB and PstP were used at 5 µM and 1 µM, respectively, and incubated 30 min at 30° C. The reaction products were resolved on a SDS-PAGE gel and the lost of labelling was visualized on the auto-radiography of the dried gel. The dephosphorylation of PknB by PstP was also simply assayed by the appearance of a lower band on a gel corresponding to dephosphorylated PknB. The reaction was carried out in 10 µl of the same buffer for 10 min at 30° C., except that PknB substrate was used at 1 µM, various concentrations of the phosphatase PstP were added from 50 to 300 nM.

Mass Spectrometry Analysis

Identification of phosphorylated sites was performed by mass measurements in whole peptide mixtures and in purified HPLC fractions of proteins digested with trypsin (Promega, 0.5 µg per 20-50 µg of protein sample in 50 mM ammonium bicarbonate buffer, pH 8.4, overnight incubation at 35° C.). Twenty-six tryptic peptides covering 90% of the $PknB_{1-279}$ sequence were thus identified (data not shown), whereas digestion peptide products smaller than five amino acid residues could not be detected. In some experiments proteins were treated with a phosphatase before proteolytic cleavage: alkaline phosphatase from Roche Diagnostics (20 enzyme units per 20-40 µg of protein incubated in an assay mixture according to instructions supplied by the manufacturer, for 1 h at 35° C.) or purified PstP enzyme as described elsewhere in this section.

MALDI-TOF MS was carried out in a Voyager DE-PRO system (Applied Biosystems) equipped with a $N_2$ laser source (λ=337 nm). Mass spectra were acquired for positive ions in linear and reflector modes at an accelerating voltage of 20 kV. The matrix was prepared with α-cyano-4-cinnamic acid for peptides or with sinnapinic acid for proteins, as saturated solutions in 0.2% trifluoroacetic acid in acetonitrile-$H_2O$ (50%, v/v). Measurement of peptide masses in reflector mode was performed under conditions of monoisotopic resolution with the accuracy close to 50 p.p.m. attained with external calibration. For this purpose a mixture of the following peptide mass standards was included ([MH]$^+$ monoisotopic mass, concentration): angiotensin I (1296.68, 2 pmol µl$^{-1}$); ACTH 1-17 clip (2093.08, 2 pmol µl$^{-1}$); ACTH 18-39 clip (2465.20, 1.5 pmol µl$^{-1}$); and ACTH 7-38 clip (3657.93, 3 pmol µl$^{-1}$). Better accuracy was obtained when internal mass calibration was sometimes performed with already characterised peptides present in PknB tryptic digests. For mass measurements of PknB proteins in linear mode, enolase of Baker's yeast (average mass of the protonated molecular ion [MH]$^+$=46.672, and [MH2]$^{+2}$=23.336) was used as a calibration standard. Samples for MS were usually prepared by spotting 0.5 µl of matrix solution and 0.5 µl of peptide solution, or tiny droplets from a desalting microcolumn eluted with matrix solution (see below), directly on the sample plate.

Selected peptides isolated from HPLC runs were sequenced by PSD-MS analysis of the y-ion series generated from the samples (Kaufmann et al., 1993, *Rapid Commun Mass Spectrom* 7: 902-910), following instructions provided by the instrument manufacturer. When additional data were required to confirm a phosphorylation site by MS sequencing, the corresponding tryptic peptide was submitted to Ba(OH)$_2$ treatment for dephosphorylation of serine or threonine residues, following published procedures (Resing et al., 1995, *Biochemistry* 34: 9477-9487).

HPLC separations were performed in a reverse-phase column (Vydac C18, 150×2.1 mm) equilibrated with 0.1% trifluoroacetic acid in $H_2O$ (solvent A), and eluted with a gradient of 0.07% trifluoroacetic acid in acetonitrile (solvent B). Chromatographic conditions were as follows: flow rate 0.2 ml min$^{-1}$; chart paper 2 mm min$^{-1}$; gradient was from 0 min to 20 min up to 10% B, from 20 min to 100 min up to 30% B, from 100 min to 110 min up to 50% B, from 110 min to 115 min up to 100% B, and then 100% B isocratic for 5 min more; detection was by UV recording at 220 nm.

Relative amounts of the tryptic peptide A162-R189 showing different degrees and patterns of phosphorylation were calculated for wild-type and mutant PknB enzymes (Table 1). Peak size of purified and identified HPLC peaks (according to MS and PSD-MS measurements) was measured and corrected according to the chromatographic response of each peptide, tested in advance under identical chromatographic conditions as described above.

For mass measurements, HPLC fractions were sometimes concentrated under a $N_2$ gas flow, freeze-dried, or immobilised on reverse-phase Poros 10 R2 beads (Applied Biosystems). The latter was also a useful procedure to desalt small peptide or protein samples in batch or in home-made microcolumns (Gobom et al., 1999, *J Mass Spectrom* 34: 105-116). Virtual tryptic digestions and other mass calculations were performed with the GPMAW32 (v.4.02) program (Lighthouse Data).

Results

PstP is a Ser/Thr Protein Phosphatase

Figure 2:
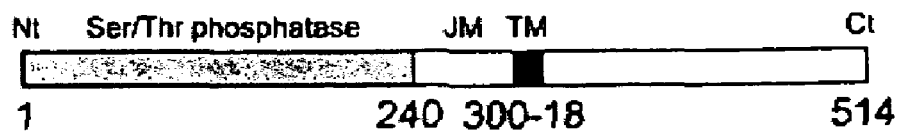
FIG. 2: A. Structural organization of PstP. JM; juxtamembrane region, TM; transmembrane region. B. Primary sequence alignment of the catalytic domain of PstP and the human PP2C (SEQ ID NOS:1 and 2) Conserved residues are boxed. The amino acids of PP2C involved in the binding of the metal ions and the phosphate are indicated with a star. Secondary structural elements are indicated above the sequence.
Figure 2B:
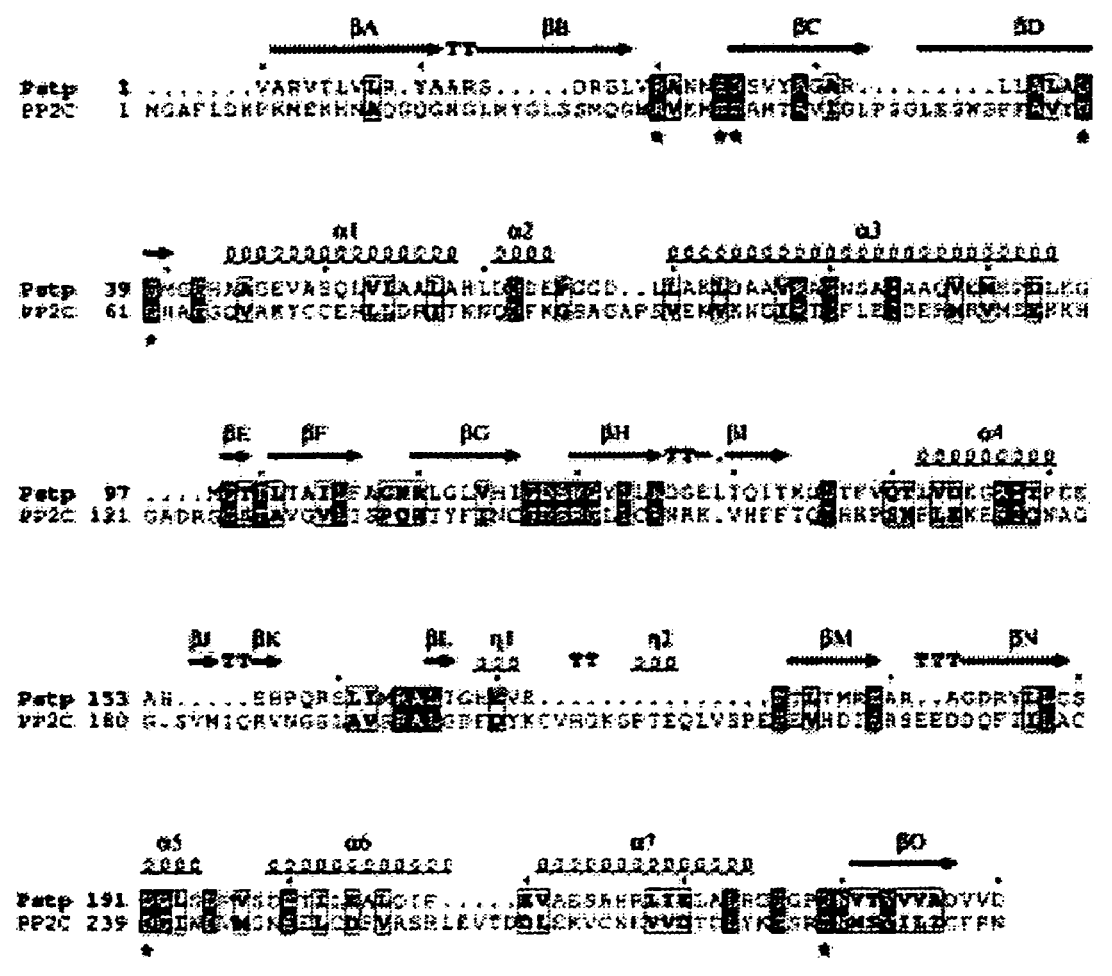

The pstP gene (Rv0018c) encodes a putative transmembrane protein of 514 aa (Cole et al., 1998, *Nature* 393: 537-544) with a C-terminal extracellular domain (196 aa) rich in proline and serine residues (FIG. 2A). The putative intracellular domain (301 aa) is homologous to members of the eukaryotic Ser/Thr protein phosphatase PPM family (Bork et al., 1996, *Protein Sci* 5: 1421-1425). The sequence alignment of the catalytic domains of PstP and human PP2C, the prototype member of the PPM family, is shown in FIG. 2B. Although PstP displays only 17% identity with the human enzyme, all the motifs corresponding to key structural elements (Bork et al., 1996, *Protein Sci* 5: 1421-1425) are present in the PstP sequence. The crystal structure of the human PP2C has revealed a metal ion-catalysed dephosphorylation mechanism (Das et al., 1996, *EMBO J* 15: 6798-6809). As indicated in FIG. 2B, all the residues involved in the binding of metal cations and phosphate are conserved in PstP, suggesting a common mechanism of phosphate recognition and catalysis.

Figure 3:
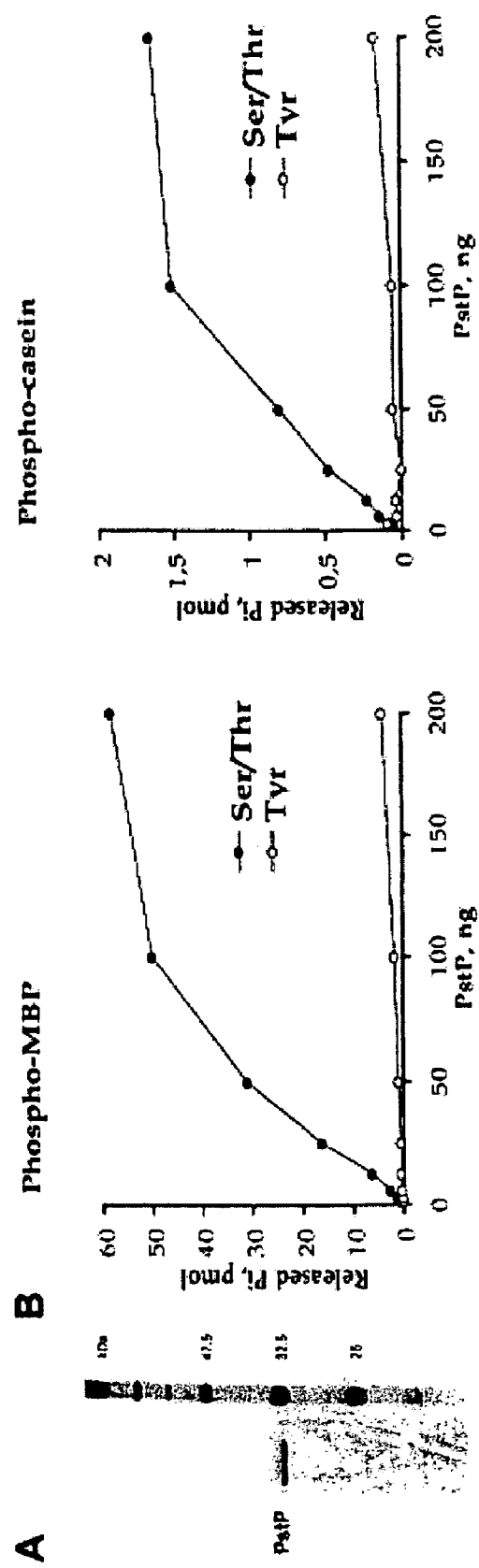
FIG. 3: A. Purification to homogeneity of $PstP_{1-240}$. His-tagged $Pstp_{1-240}$ was purified by affinity and size exclusion chromatography. The purity was then checked by SDS-PAGE electrophoresis. $PstP_{1-240}$ appears as a single discrete band on the gel with an apparent MW (32 kDa) slightly higher than the expected value (27.6 kDa).

The multiple alignment of PstP with other members of the PPM phosphatase family predicted Asp 240 as the last residue of the catalytic domain. Thus, the His-tagged construction PstP$_{1-240}$ was produced as a soluble protein in *E. coli* (FIG. 3A). The protein phosphatase activity and the specificity towards phospho-amino acids were tested using different substrates. The myelin basic protein (MBP) and α-casein were phosphorylated either on serine and threonine residues with the protein kinase A (PKA) or on tyrosine residues with the Abl kinase using radiolabelled ATP. As shown in FIG. 3B, PstP dephosphorylated phopho-Ser/Thr substrates but showed little or no activity with phospho-Tyr substrates. Furthermore, PstP phosphatase activity was strictly dependent on divalent cations with a preference for $Mn^{2+}$ versus $Mg^{2+}$ (data not shown). Thus, in agreement with sequence homology-based predictions, these results demonstrate that the intracellular region of PstP is a Ser/Thr protein phosphatase that belongs to the PPM family.

Figure 4A:
Figure 4B:
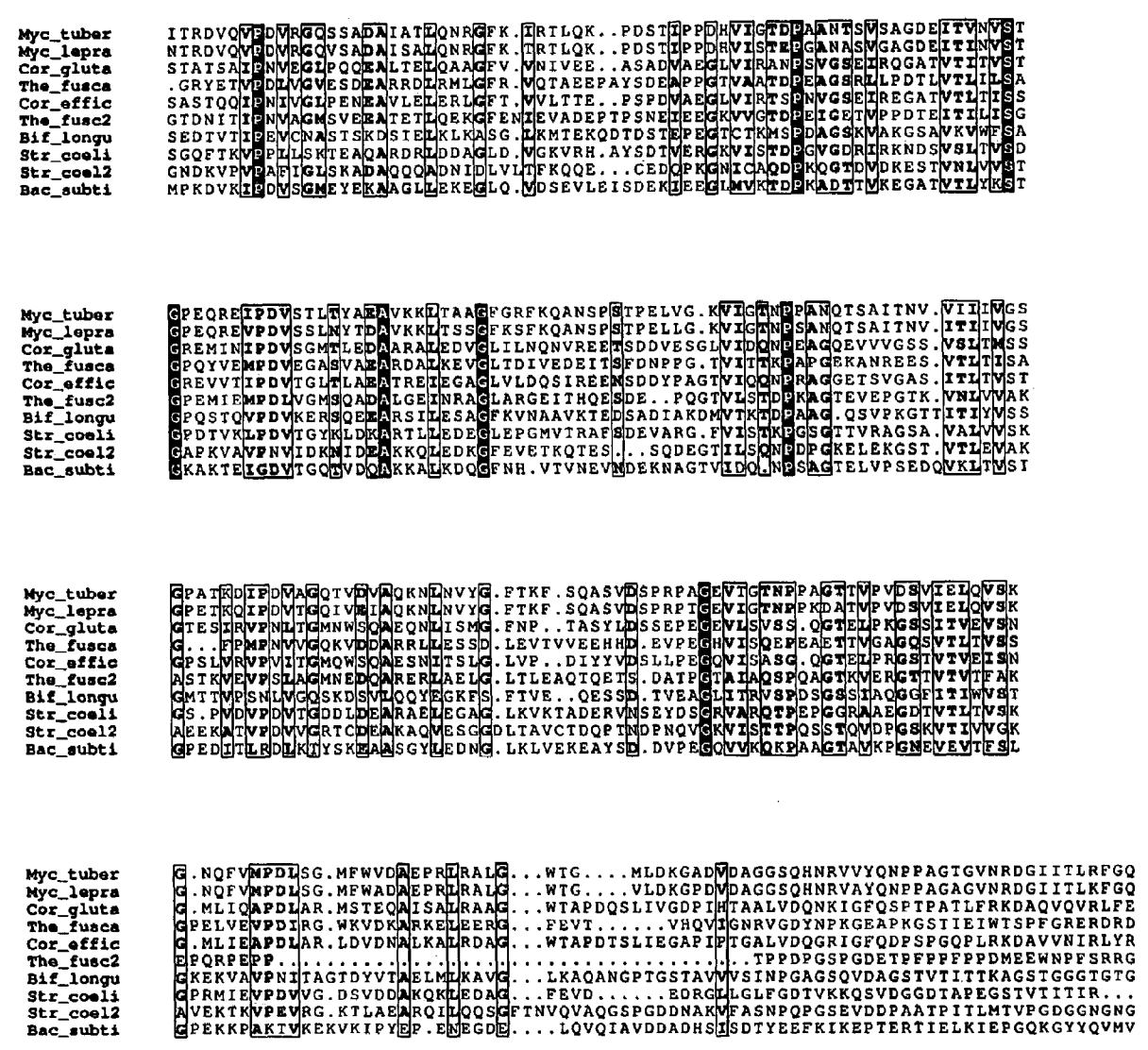

The C-Terminal Domain of PknB is Similar to that Found in Various Other Bacterial STPKs PknB is predicted to be a 626 aa transmembrane protein with an intracellular N-terminal kinase domain (331 aa) and an extracellular C-terminal domain (276 aa) (FIG. 4A). This structural organization for STPKs is found in plants and as receptors for the transforming growth factor β(TGFβ) family cytokines in vertebrates, where the C-terminal domain is a signal sensor. This could also be the case for the transmembrane STPKs from prokaryotes. The C-terminal domain of PknB shows some degree of sequence similarity with the C-terminal domain of several prokaryotic STPKs, including actinobacteria (*corynebacterium, streptomyces, bifidobacterium*) and other Gram-positive bacteria (*listeria, bacillus, streptococcus*) (FIG. 4B). These proteins display a diverse number of copies, four in PknB, of the recently described PASTA domain (for penicillin-binding-protein and serine/threonine kinase associated domain, Yeats et al., 2002, *TIBS* 27: 438-440). This suggests that all these kinases could respond to a similar type of ligand. Actually, it has been speculated that the PASTA domains could bind unlinked peptidoglycan (Yeats et al., 2002, *TIBS* 27: 438-440), although no experimental evidence is available to substantiate this claim. It is noteworthy that a gene coding for a putative Ser/Thr protein phosphatase is found in the same genomic region for the above mentioned organisms, suggesting a functional association with the STPK. Indeed, it has recently been described that the PrkC kinase and the PrpC phosphatase from *Bacillus subtilis* form such a couple in vivo with opposite effects on stationary-phase physiology (Gaidenko et al., 2002, *J Bacteriol* 184: 6109-6114).

The Catalytic Domain of PknB is a Functional Protein Kinase

The full-length recombinant PknB protein has been previously characterized and shown to possess STPK activity (Av-Gay et al., 1999, *Infect Immun* 67: 5676-5682). To allow detailed biochemical and structural studies, we have chosen to focus on its catalytic domain. Multiple sequence alignment with members of the Ser/Thr protein kinase family and homology modelling based on available three-dimensional structures pointed to Gly 279 as the last residue in the C-terminal α-helix of the catalytic domain. Thus, the domain corresponding to amino acid residues 1-279 of PknB (PknB$_{1-279}$) has been produced in *E. coli* as a soluble, monomeric His-tagged protein (FIG. 5A).

The kinase activity of PknB$_{1-279}$ was tested either in an autophosphorylation assay or using MBP as a model substrate. Like the full-length renatured PknB (Av-Gay et al., 1999, *Infect Immun* 67: 5676-5682), PknB$_{1-279}$ autophosphorylates and phosphorylates MBP (FIG. 5A). Thrombin-digested PknB$_{1-279}$ (i.e. without the His-Tag) is also autophosphorylated, indicating that specific autophosphorylation sites exist on the PknB catalytic domain (data not shown). Kinase activity depends on divalent cations (FIG. 5A), PknB$_{1-279}$ showing a clear preference for $Mn^{2+}$ versus $Mg^{2+}$ ions (FIG. 5B). These observations demonstrate that, when separately expressed, the catalytic domain of PknB has intrinsic kinase activity, implying that other regions of the protein (such as the juxtamembrane region) are not required to stabilize an active conformation.

The recently determined structure of the catalytic core of PknB in complex with nucleotide at 2.2 Å resolution (Ortiz-Lombardía et al., 2003, *J Biol Chem* 278: 13094-13100) and 3 Å resolution (Young et al., 2003, *Nature Struct Biol* 10: 168-174) lends further support to these observations. The PknB catalytic domain was found to be very similar to its eukaryotic homologues and shares a number of essential hallmarks first described for PKA (Knighton et al., 1991, *Science* 253: 407-414). In particular, all amino acid residues and other structural elements important for catalysis are found in their active conformation (Ortiz-Lombardía et al., 2003, *J Biol Chem* 278: 13094-13100).

Different preparations of PknB$_{1-279}$ produced a relatively broad complex mass peak in MALDI-TOF mass spectrometry experiments, with maximum intensity at m/z=32 538 and smaller signals close to 80 Da, 98 Da or 160 Da apart (data not shown). After treatment with PstP or alkaline phosphatase, the peak shifted to m/z=32 291 (the sequence-predicted average mass of uncleaved PknB$_{1-279}$ is 32 281 Da), indicating the removal of at least three phosphate groups linked to the protein (FIG. 6). However, we have failed to detect any phosphorylated residue in the 3D structure of PknB (Ortiz-Lombardía et al., 2003, *J Biol Chem* 278: 13094-13100). As the whole catalytic domain (except for residues A164-T179 covering most of the activation loop) is well-defined in the electron density map, this suggests that the putative phosphoresidues should be found in the disordered or mobile parts of the protein, i.e. at the N-terminal peptide extension outside the catalytic core and/or within the activation loop itself, in agreement with the putative phosphorylation sites recently proposed for this region by Young et al. (2003, *Nature Struct Biol* 10: 168-174).

PstP Dephosphorylates PknB and Inhibits its Kinase Activity

Full-length PknB has been shown to be autophosphorylated on Ser and Thr residues (Av-Gay et al., 1999, *Infect Immun* 67: 5676-5682), and the question arises whether PknB$_{1-279}$ could be a substrate for PstP. To address this possibility, PknB$_{1-279}$ was autophosphorylated with radioactive ATP before incubation with PstP in the presence or absence of MnCl$_2$. As shown in FIG. 7A, PstP is capable of dephosphorylating PknB. Phosphate hydrolysis is also reflected by the shift in PknB migration on the gel concomitant with loss of label, the lower band corresponding to dephosphorylated PknB. These differences in gel mobility were exploited to further monitor the phosphatase reaction without previous radioactive labelling (FIG. 7B). The dephosphorylation of PknB by PstP also indicates that the recombinant kinase produced in *E. coli* is phosphorylated in vivo.

We then asked whether the dephosphorylation of PknB could have an effect on its kinase activity. To address this question, PknB was preincubated with Pstp and ATP was replaced by thio-γATP in the kinase reaction. The rational for this assay resides in the ability of PknB of thiophosphorylating substrates whereas PstP is not active on these thiophosphosubstrates (data not shown). Under these conditions, the kinase activity can be measured without interference from the phosphatase activity. FIG. 7C shows that prior dephosphorylation of PknB by PstP inhibits kinase activity on MBP. These results strongly suggest that the phosphorylation state of PknB is important in maintaining a fully active kinase.

Identification of Two Phosphothreonines in the Activation Loop of PknB

Figures 8A, 8B, 8C:
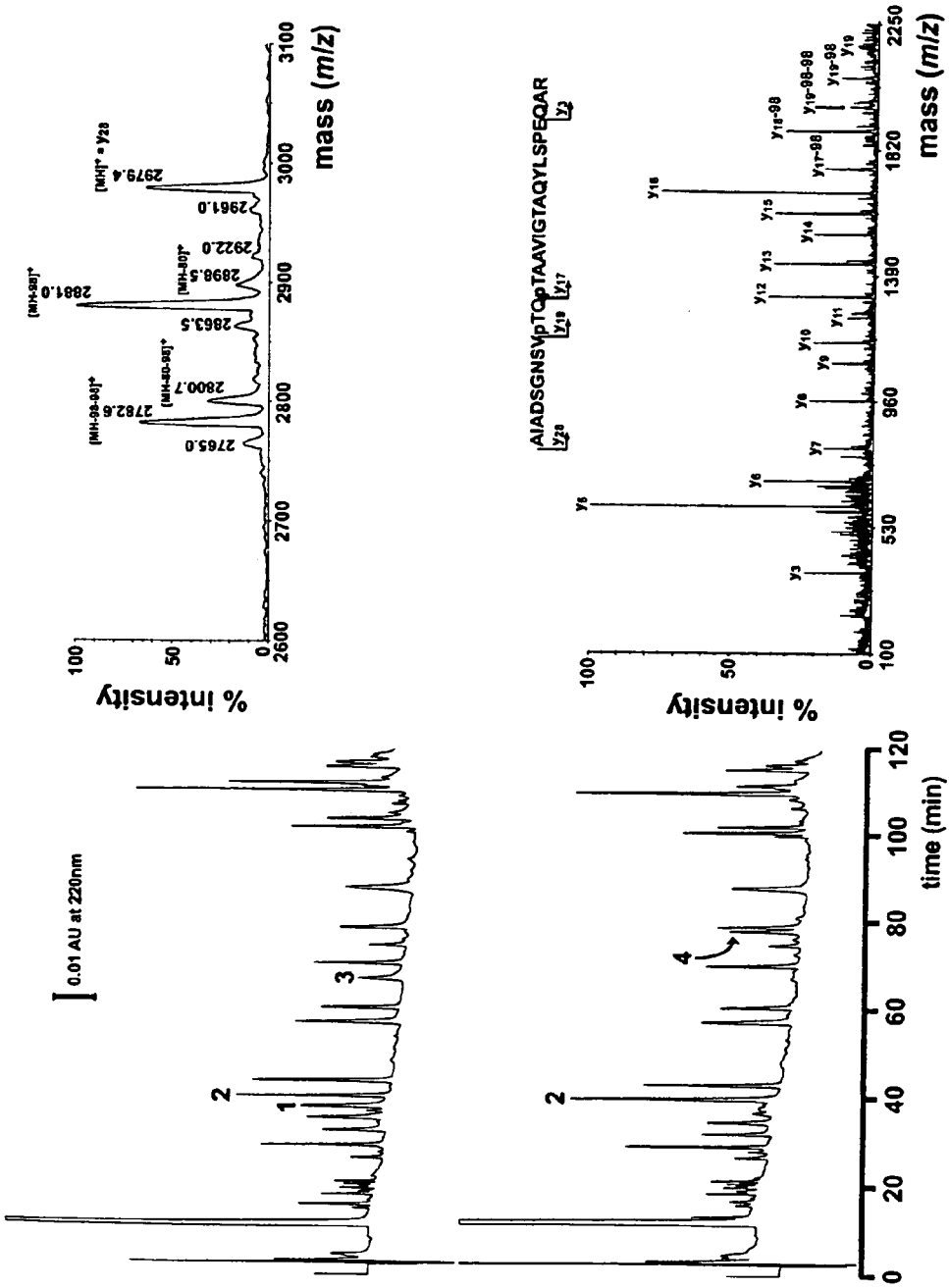

Mass spectrometry was used to identify the phosphoresidues detected in PknB$_{1-279}$. Comparison of the reverse-phase chromatograms of the trypsin digestion products of either PknB$_{1-279}$ or PstP-treated PknB$_{1-279}$ (covering 90% of the PknB$_{1-279}$ sequence) revealed changes in the elution pattern of some selected peptides (FIG. 8A). This observation was consistent with results from MS, in both reflector and linear modes, obtained from the corresponding whole peptide mixture (data not shown). In linear mode, two phosphopeptides could be identified from untreated PknB$_{1-279}$. A signal at m/z=1850.1 was assigned to the His-tag peptide plus one phosphate group (calc. average mass=1849.9 for the [MH]$^+$ peptide), and a strong signal at m/z=2981.3 was assigned to the di-phosphorylated tryptic peptide A162-R189 (calc. mass=2981.0), which includes a large fraction of the activation loop. It is noteworthy that no MS signal was detected for the non-phosphorylated A162-R189 peptide (calc. mass=2821.1), except when PknB$_{1-279}$ was pretreated with a phosphatase such as alkaline phosphatase or PstP. Only in such conditions a prominent mass signal (at m/z=2820.8) was observed in both linear and reflector modes.

These results were further confirmed when the separate peptide fractions were identified by MS measurements in reflector mode. Thus, peaks numbered 1 and 2 (FIG. 8A) were assigned to the monophosphorylated and unphosphorylated His-tag peptide, respectively, whereas peak 3 was assigned to the diphosphorylated A162-R189 peptide. Upon treatment with PstP, peak 1 was reduced in size, peak 2 increased and peak 3 almost disappeared, presumably giving rise to peak 4, which corresponds to the unphosphorylated A162-R189 peptide.

Post-source decay mass spectrometry (PSD-MS) measurement of a sample from peak 3 confirmed the presence of two phosphate groups in this peptide (FIG. 8B). Definitive identification and localization of the phosphorylated residues was achieved by PSD-MS sequencing of HPLC peak 3 purified from independent batches of PknB. This analysis showed that A162-R189 peptide was phosphorylated on Thr 171 and Thr 173 (FIG. 8C). In all cases, phosphorylation of these sites was close to 100%, indicating that these threonines are systematically and homogeneously linked to a phosphate. The HPLC patterns of PknB tryptic digests were extremely constant and reproducible over the time and with different preparations of the protein. However, in some experiments a shoulder or even a small peak (just before peak 3 in FIG. 8A) could be observed, with a m/z=3061.1 (data not shown). This was identified as a triphosphorylated species of the A162-R189 peptide (calc. mass=3061.3). The third phosphosite is a serine that could not be unambiguously identified by sequencing and could correspond to either Ser 166 or Ser 169.

The above MS results identify two threonine residues from the activation loop, Thr 171 and Thr 173, as targets for PknB autophosphorylation and PstP dephosphorylation. These residues are part of a disordered region in the two PknB crystal structures (Ortiz-Lombardía et al., 2003, *J Biol Chem* 278: 13094-13100; Young et al., 2003, *Nature Struct Biol* 10: 168-174). However, inspection of the charge distribution at the molecular surface of the protein reveals an exposed cluster of basic residues that are favourably positioned to provide an anchoring site for the phosphothreonine residues (FIG. 9A). These arginine residues have partially disordered or mobile side-chains in the crystal structure, probably reflecting the absence of bound substrate. When compared with a similar cluster in PKA (Knighton et al., 1991, *Science* 253: 407-414) that binds phospho-Thr 197 in the activation loop (FIG. 9B), the positively charged region in PknB is found to cover a more extended surface area, raising the possibility of this region binding the phosphate groups of both Thr 171 and Thr 173.

Activation Loop Mutants of PknB

To confirm and further analyse the role of the identified phospho-threonines in PknB kinase activity, these residues were mutated to alanine, singly or in combination. The single mutants T171A, T173A and the double mutant T171/

173 A were produced and analysed in the MBP phosphorylation assay. Comparison of the kinetics of phosphorylation of MBP by the mutants (FIG. 10) shows that the kinase activity is affected by each single mutation to a similar extent, being 15- and 20-times less active than PknB respectively. The double mutant is 300-fold less active, suggesting a combined effect of the two phosphothreonines on kinase activity. These results confirm that double phosphorylation of the activation loop is required for full kinase activity and demonstrate unambiguously the involvement of both phosphothreonines.

These mutants were also tested for the presence and localization of phosphorylated amino acid residues and the degree of phosphorylation at each site, following the same experimental protocol described above for the wild-type enzyme (Table 1). The N-terminal His-tag peptide showed a consistently lower degree of phosphorylation in the three mutants when compared to the wild-type enzyme, reflecting the lower activity of the mutants. As for the wild-type enzyme, the mutant T171A is mainly diphosphorylated in the activation loop, the residues involved being now Ser 169 and Thr 173. However, phosphorylation of Ser 169 does not restore wild-type activity and seems to play no functional role. On the other hand, the T173A mutant appears to be mainly monophosphorylated in Thr 171 (a much smaller HPLC signal could be assigned to a diphosphorylated species at residues Thr 171 and either Ser 166 or Ser 169). Analysis of peptides from the trypsin-digested double mutant T171/173 A demonstrated the occurrence of unphosphorylated (36%) and one monophosphorylated (at either Ser 166 or Ser 169) A162-R189 peptide species. In summary, both single mutants appear still fully phosphorylated on the remaining threonine and the activity decrease of the single and double mutants did not show co-operative behaviour, suggesting that Thr 171 and Thr 173 are independent phospho-sites. Moreover, a similar decrease in kinase activity is observed upon the lost of each phosphosite, suggesting that the two phosphothreonines are equally important for PknB activity.

TABLE 1

| Protein | Phosphorylation status[a] and amino acid(s) involved[b] | | |
|---|---|---|---|
| | His-Tag peptide | Peptide S162-R189 | Phosphorylated residues |
| PknB_[c] | 45-60% non-P | close to 100% di-P | Thr171 and Thr173 |
| | 40-55% mono-P | trace of tri-P[d] | Thr171, Thr173 and (Ser169 or Ser166) |
| T171A | 82% non-P | close to 100% di-P | Thr173 and Ser169 |
| | 18% mono-P | | |
| T173A | 87% non-P | 96% mono-P | Thr171 |
| | 13% mono-P | 4% di-P | Thr171 and (Ser169 or Ser166) |
| T171/173 A | 89% non-P | 36% non-P | — |
| | 11% mono-P | 64% mono-P | (Ser169 or Ser166) |

[a] Refers to relative amounts of phosphorylated species present in Nt His-Tag peptide or in peptide S162-R189 populations. Non-P, mono-P, di-P or tri-P indicates absence, one, two or three phosphate groups present respectively. Peptide samples were isolated and quantified after protein treatment with trypsin followed by HPLC and peak identification by MS, as mainly described in FIG. 8 and in Experimental procedures.
[b] Modified amino acid(s) by phosphorylation were localized in the sequence S162-R189 by PSD-MS as exemplified in FIG. 8B and C following the protocols described in Experimental procedures. The phosphorylated serine of the Nt His-Tag peptide (MGSSHHHHHHSSGLVPR) was not identified.

TABLE 1-continued

| Protein | Phosphorylation status[a] and amino acid(s) involved[b] | | |
|---|---|---|---|
| | His-Tag peptide | Peptide S162-R189 | Phosphorylated residues |

[c] Samples from three independently produced batches of $PknB_{1-279}$ were tested.
[d] The phosphorylation of the third residue in the activation loop, Ser 169 or Ser 166, appears of minor importance, as the degree of phosphorylation detected was systematically low or nul.

Although *M. tuberculosis* encodes 11 STPKs (Cole et al., 1998, *Nature* 393: 537-544) there is only one clear serine/threonine protein phosphatase, PstP which is a member of the PPM family (Bork et al., 1996, *Protein Sci* 5: 1421-1425). We show here that its catalytic domain, $PstP_{1-240}$, dephosphorylates substrates previously phosphorylated on serine or threonine but not on tyrosine residues. Furthermore, its activity is strictly dependent on $Mn^{2+}$ or $Mg^{2+}$ ions, which is consistent with the deduced metal-ion catalysed dephosphorylation mechanism for this family (Das et al., 1996, *EMBO J* 15: 6798-6809).

On the basis of its amino acid sequence, PknB (and all other mycobacterial STPKs) have been classified in the Pkn2 family of prokaryotic STPKs (Leonard et al., 1998, *Genome Res* 8: 1038-1047), the cluster that most closely resembles their eukaryotic counterparts and that could have arisen by early horizontal transfer from eukarya to bacteria with complex development cycles. Recombinant full-length PknB has already been shown to possess kinase activity and autophosphorylation sites on both serine and threonine residues (Av-Gay et al., 1999, *Infect Immun* 67: 5676-5682). Here we studied a construct limited to the catalytic core domain, $PknB_{1-279}$, as defined by sequence homology. We found that this construct is an active kinase showing that the juxtamembrane region is not required for activity, although it may still be involved in further stabilization or activity regulation (see below).

Various mechanisms of eukaryotic protein kinase regulation have been described (Johnson et al., 1996, *Cell* 85: 149-158; Hubbard and Till, 2000, *Annu Rev Biochem* 69: 373-398; Huse and Kuriyan, 2002, *Cell* 109: 275-282). The transition between active and inactive forms may occur via control of access to the catalytic and/or the substrate-binding site, or by rearrangement of structural elements involved in catalysis or substrate recognition. Furthermore, interaction with other protein domains or cofactors may take place. It is noteworthy that a large number of these regulation mechanisms involve phosphorylation/dephosphorylation (inside or outside the catalytic domain) through an autocatalytic mechanism or by the action of other intervening kinases and phosphatases.

The present study shows that the catalytic domain of PknB autophosphorylates in vitro and is phosphorylated when expressed in *E. coli*. To see whether PknB autophosphorylation could play a regulatory role, we first identified phosphorylated residues in PknB. Mass spectrometry analysis indicated that two threonine residues of the activation loop (Thr 171 and Thr 173) are systematically phosphorylated (presumably autophosphorylated). Other eukaryotic protein kinases also display two phosphorylation sites in their activation loops, such as MKK1 (two Ser residues, Alessi et al., 1994, *EMBO J* 0: 1610-1619) or ERK2 (a Thr and a Tyr residues, both of which have to be phosphorylated to form the active enzyme, Robbins et al., 1993, *J Biol Chem* 268: 5097-5106). The activation loop is a major control element of an active/inactive conformational switch in numerous kinases (Steinberg et al., 1993, *Mol Cell Biol* 13: 2332-2341; Johnson et al., 1996, *Cell* 85: 149-158; Huse and Kuriyan, 2002, *Cell* 109: 275-282) whose conformation often depends on their phosphorylation state (Johnson et al., 1996 *Cell* 85: 149-158). From its structural location, this loop may control both the accessibility to the catalytic site and the binding of the substrate. A broad range of regulatory properties has been assigned to this loop, such as contributing to the proper alignment of the catalytic residues, correcting the relative orientation of the two lobes, permitting substrate binding and/or stimulating ATP binding (Huse and Kuriyan, 2002 *Cell* 109: 275-282).

The inhibitory effect of dephosphorylation of PknB on its kinase activity shows that phosphorylation is required for full activity. This is further confirmed by the mutagenesis study of activation loop threonine residues. Compared to the wild-type enzyme, the two single mutants, still phosphorylated on the remaining threonine, display comparable, reduced activities whereas the double-mutation further decreases the activity. Hence, Thr 171 and Thr 173 play independent and equivalent but complementary roles to reach maximal kinase activity.

The structural role of the phosphothreonine residues in PknB remains unexplained because the activation loop is disordered in the crystal structures (Ortiz-Lombardía et al., 2003 *J Biol Chem* 278: 13094-13100; Young et al., 2003 *Nature Struct Biol* 10: 168-174). This is not unusual in kinase structures. It has been observed both in active and inactive kinases, and does not indicate a particular phosphorylation state. In some kinases, phosphorylation of the loop fixes its conformation (Johnson et al., 1996 *Cell* 85: 149-158) and disorder could thus indicate partial phosphorylation. However, this does not seem to be the case for PknB as the activation loop has no defined structure in the crystal structure despite complete phosphorylation of both threonines. Instead, stabilization of the PknB loop could occur upon the binding of the peptide substrate through an induced-fit mechanism or by additional intra- or intermolecular interactions with other factors outside the kinase core. In any case, a positively charged region is observed in the PknB structure at the expected phosphothreonine-binding site, equivalent to a similar cluster that in PKA binds the single phosphorylated threonine, Thr197 (FIG. 9).

Taken together, these results strongly suggest that PknB kinase activity can be regulated by the state of phosphorylation of its activation loop in vivo through an autophosphorylation mechanism. Interesting observations can be drawn from the inspection of the activation loop sequences from the other *M. tuberculosis* STPKs. One or both threonines are conserved in all but two STPKs (PknG and PknI have shorter loops) suggesting that these enzymes should also be regulated by autophosphorylation in their activation loops. Thus, besides the same overall 3D structure and catalytic mechanism, eukaryotic and prokaryotic kinases would also share this mechanism of regulation, in spite of previous claims suggesting the absence of this process in prokaryotes (Motley and Lory, 1999 *Infect Immun* 67: 5386-5394). Further investigations are obviously required to determine the physiological relevance of PknB dephosphorylation by PstP and the effect of this protein phosphatase on other kinases, in particular PknA which is present in the same operon.

Other mechanisms of kinase regulation could exist. PknB is presumed to be a transmembrane protein with a putative external ligand binding domain, an organization similar to that found in sensor histidine kinases (Parkinson, 1993 *Cell* 73: 857-871) and receptor tyrosine kinases (Schlessinger, 2000 *Cell* 103: 211-225). Binding of a ligand to the extracellular domain of the latter usually promotes receptor dimerization and/or a structural rearrangement that induces autophosphorylation and hence activation of the kinase domain. Interestingly, dimerization has recently been reported for PrkC (Madec et al., 2002 *Mol Microbiol* 46: 571-586), a transmembrane STPK from *B. subtilis* with homology to PknB both in its Nt and Ct domains (FIG. 4B). Another regulation mechanism, described for both the type I TGF-β receptor serine/threonine kinase (Huse et al., 1999 *Cell* 96: 425-436) and the ephrin receptor tyrosine kinase (EphB2)(Wybenga-Groot et al., 2001 *Cell* 106: 745-757), involves the maintenance of an inactive state via the interaction of the juxtamembrane region with the kinase domain. Upon ligand stimulation of EphB2, the autophosphorylation of Tyr residues in the juxtamembrane sequence releases the inhibition and renders this sequence available for further interaction with SH2 domains of target proteins (Wybenga-Groot et al., 2001 *Cell* 106: 745-757). The juxtamembrane region is missing in PknB$_{1-279}$. A recombinant construct of PknB corresponding to the catalytic core of the kinase plus the juxtamembrane sequence was also produced (see Experimental procedures). Three phosphorylation sites including Thr 294 and Thr 309 were identified in the juxtamembrane sequence (data not shown).

Obviously, numerous modifications and variations of the present invention are possible in light of the above teachings. It is therefore to be understood that within the scope of the appended claims, the invention may be practiced otherwise than as specifically described herein.

The invention claimed is:

1. A method for identifying a substance which modulates the activity of a pknB protein kinase via its interaction with a ptsp2 phosphatase, comprising contacting a recombinant bacterial cell with the substance, wherein the recombinant bacterial cell comprises one or more vectors encoding the pknB protein kinase and the pstp2 phosphatase and wherein the recombinant bacterial cell expresses the pknB protein kinase and the pstp2 phosphatase, and wherein the pknB protein kinase consists of amino acids 1 to 279 of pknB protein kinase from *M. tuberculosis* or an amino acid sequence having at least 95% sequence identity to amino acids 1 to 279 of pknB protein kinase from *M. tuberculosis* and has protein kinase activity, and the pstp2 phosphatase comprises the amino acid sequence in SEQ ID NO:1 or an amino acid sequence that is at least 95% identical to SEQ ID NO:1 and that has phosphatase activity;

measuring the pknB protein kinase activity in said bacterial cell; and comparing the pknB protein kinase activity in the recombinant bacterial cell contacted with the substance to a bacterial cell which has not been contacted with the substance, wherein a change in protein kinase activity in the recombinant bacterial cell contacted with the substance relative to the pknB kinase activity in the bacterial cell which has not been contacted with the substance indicates that the substance modulates the activity of pknB protein kinase via its interaction with the pstp2 phosphatase.

2. The method of claim 1, wherein the pknB protein kinase consists of amino acids 1 to 279 of pknB protein kinase from *M. tuberculosis*.

3. The method of claim 1, wherein the pknB protein kinase consists of an amino acid sequence having at least 95% sequence identity to amino acids 1 to 279 of pknB protein kinase from *M. tuberculosis* and has protein kinase activity.

4. The method of claim 3, wherein the pknB consists of an amino acid sequence having at least 97% sequence identity to amino acids 1 to 279 of pknB protein kinase from *M. tuberculosis* and has protein kinase activity.

5. The method of claim 3, wherein the pknB consists of an amino acid sequence having at least 99% sequence identity to amino acids 1 to 279 of pknB protein kinase from *M. tuberculosis* and has protein kinase activity.

6. A method of identifying an antibacterial substance, comprising identifying a substance according to claim 1; and contacting a bacterial cell with the substance; and comparing the growth, the survival or both of the bacterial cell contacted with the substance according to claim 1 to a bacterial cell that has not been contacted with the substance, wherein a reduction in the growth, survival or both of the bacterial cell contacted with the substance is indicative that the substance is an antibacterial substance.

7. A method of identifying an antibacterial substance, comprising identifying a substance according to claim 2; and contacting a bacterial cell with the substance; and comparing the growth, the survival or both of the bacterial cell contacted with the substance according to claim 2 to a bacterial cell that has not been contacted with the substance, wherein a reduction in the growth, survival or both of the bacterial cell contacted with the substance is indicative that the substance is an antibacterial substance.

8. A method of identifying an antibacterial substance, comprising identifying a substance according to claim 3; and contacting a bacterial cell with the substance; and comparing the growth, the survival or both of the bacterial cell contacted with the substance according to claim 3 to a bacterial cell that has not been contacted with the substance, wherein a reduction in the growth, survival or both of the bacterial cell contacted with the substance is indicative that the substance is an antibacterial substance.

9. A method of identifying an antibacterial substance, comprising identifying a substance according to claim 4; and contacting a bacterial cell with the substance; and comparing the growth, the survival or both of the bacterial cell contacted with the substance according to claim 4 to a bacterial cell that has not been contacted with the substance, wherein a reduction in the growth, survival or both of the bacterial cell contacted with the substance is indicative that the substance is an antibacterial substance.

10. A method of identifying an antibacterial substance, comprising identifying a substance according to claim 5; and contacting a bacterial cell with the substance; and comparing the growth, the survival or both of the bacterial cell contacted with the substance according to claim 5 to a bacterial cell that has not been contacted with the substance, wherein a reduction in the growth, survival or both of the bacterial cell contacted with the substance is indicative that the substance is an antibacterial substance.

11. The method of claim 1, wherein the pstp2 phosphatase comprises SEQ ID NO:1.

12. The method of claim 1, wherein the pstp2 phosphatase comprises an amino acid sequence that is at least 95% identical to SEQ ID NO:1.

* * * * *